US011738026B2

(12) United States Patent
Chen et al.

(10) Patent No.: US 11,738,026 B2
(45) Date of Patent: Aug. 29, 2023

(54) COMBINATION THERAPY COMPRISING AN ALK2 INHIBITOR AND A JAK2 INHIBITOR

(71) Applicant: INCYTE CORPORATION, Wilmington, DE (US)

(72) Inventors: Yaoyu Chen, Newark, DE (US); Matthew C. Stubbs, Woolwich, NJ (US); Ying-Nan Pan Chen, Wilmington, DE (US); Michelle Pusey, Wilmington, DE (US)

(73) Assignee: INCYTE CORPORATION, Wilmington, DE (US)

( * ) Notice: Subject to any disclaimer, the term of this patent is extended or adjusted under 35 U.S.C. 154(b) by 266 days.

(21) Appl. No.: 16/953,989

(22) Filed: Nov. 20, 2020

(65) Prior Publication Data

US 2021/0154195 A1 May 27, 2021

Related U.S. Application Data

(60) Provisional application No. 62/939,241, filed on Nov. 22, 2019, provisional application No. 62/980,562, filed on Feb. 24, 2020, provisional application No. 63/035,194, filed on Jun. 5, 2020, provisional application No. 63/056,768, filed on Jul. 27, 2020.

(51) Int. Cl.
*A61K 31/519* (2006.01)
*A61K 31/4439* (2006.01)
*A61P 35/02* (2006.01)

(52) U.S. Cl.
CPC ........ *A61K 31/519* (2013.01); *A61K 31/4439* (2013.01); *A61P 35/02* (2018.01)

(58) Field of Classification Search
CPC .... A61P 35/02; A61K 31/519; A61K 31/4439
See application file for complete search history.

(56) References Cited

U.S. PATENT DOCUMENTS

| | | | |
|---|---|---|---|
| 3,832,460 A | 8/1974 | Kosti | |
| 4,140,755 A | 2/1979 | Sheth et al. | |
| 5,077,290 A | 12/1991 | Fisher et al. | |
| 5,795,909 A | 8/1998 | Shashoua et al. | |
| 6,090,812 A | 7/2000 | Feenstra et al. | |
| 6,624,138 B1 | 9/2003 | Sung et al. | |
| 6,713,089 B1 | 3/2004 | Bertelsen et al. | |
| 6,852,727 B2 | 2/2005 | Goulet et al. | |
| 6,953,776 B2 | 10/2005 | Di Napoli | |
| 7,005,436 B2 | 2/2006 | Lloyd et al. | |
| 7,138,423 B2 | 11/2006 | Wu et al. | |
| 7,167,750 B2 | 1/2007 | Knudson et al. | |
| 7,265,108 B2 | 9/2007 | Ozaki | |
| 7,335,667 B2 | 2/2008 | Rodgers et al. | |
| 7,358,225 B2 | 4/2008 | Nakamura | |
| 7,517,870 B2 | 4/2009 | Auricchio | |
| 7,598,257 B2 | 10/2009 | Rodgers et al. | |
| 7,750,007 B2 | 7/2010 | Bearss et al. | |
| 7,834,022 B2 | 11/2010 | Rodgers et al. | |
| 8,053,433 B2 | 11/2011 | Rodgers et al. | |
| 8,158,616 B2 | 4/2012 | Rodgers et al. | |
| 8,309,718 B2 | 11/2012 | Li et al. | |
| 8,410,265 B2 | 4/2013 | Zhou et al. | |
| 8,420,629 B2 | 4/2013 | Rodgers et al. | |
| 8,445,488 B2 | 5/2013 | Rodgers et al. | |
| 8,486,902 B2 | 7/2013 | Rodgers et al. | |
| 8,563,541 B2 | 10/2013 | Arvanitis et al. | |
| 8,604,043 B2 | 12/2013 | Li et al. | |
| 8,691,807 B2 | 4/2014 | Yao et al. | |
| 8,716,303 B2 | 5/2014 | Rodgers et al. | |
| 8,722,693 B2 | 5/2014 | Rodgers et al. | |
| 8,741,895 B2 | 6/2014 | Rodgers et al. | |
| 8,748,401 B2 | 6/2014 | Rodgers et al. | |
| 8,765,734 B2 | 7/2014 | Huang et al. | |
| 8,829,013 B1 | 9/2014 | Rodgers et al. | |
| 8,835,423 B2 | 9/2014 | Arvanitis et al. | |
| 8,841,318 B2 | 9/2014 | Arvanitis et al. | |
| 8,933,085 B2 | 1/2015 | Rodgers et al. | |
| 8,933,095 B2 | 1/2015 | Dounay et al. | |
| 9,023,840 B2 | 5/2015 | Yao et al. | |
| 9,034,884 B2 | 5/2015 | Rodgers et al. | |
| 9,090,611 B2 | 7/2015 | Rodgers et al. | |
| 9,193,733 B2 | 11/2015 | Rodgers et al. | |
| 9,216,984 B2 | 12/2015 | Zhou et al. | |
| 9,249,145 B2 | 2/2016 | Rodgers et al. | |
| 9,249,149 B2 | 2/2016 | Silverman et al. | |
| 9,334,274 B2 | 5/2016 | Rodgers et al. | |

(Continued)

FOREIGN PATENT DOCUMENTS

EP 1875912 A1 1/2008
WO WO 1999/065909 12/1999

(Continued)

OTHER PUBLICATIONS

U.S. Appl. No. 12/137,892 / 2008/0312259, Jun. 12, 2008 / Dec. 18, 2008, James D. Rodgers.
U.S. Appl. No. 14/097,588 / 2014/0094476 / U.S. Pat. No. 8,722,693, Dec. 5, 2013 / Apr. 3, 2014 / May 13, 2014, James D. Rodgers.
U.S. Appl. No. 14/097,598 / 2014/0094477, Dec. 5, 2013 / Apr. 3, 2014, James D. Rodgers.
U.S. Appl. No. 14/256,311 / U.S. Pat. No. 8,829,013, Apr. 18, 2014 / Sep. 9, 2014, James D. Rodgers.
U.S. Appl. No. 14/256,383 / U.S. Pat. No. 8,822,481, Apr. 18, 2014 / Sep. 2, 2014, James D. Rodgers.
U.S. Appl. No. 14/270,915 / 2014/0303196 / U.S. Pat. No. 9,376,439, May 6, 2014 / Oct. 9, 2014 / Jun. 28, 2016, James D. Rodgers.
U.S. Appl. No. 15/164,518 / 2016/0339031 / U.S. Pat. No. 10,016,429, May 25, 2016 / Nov. 24, 2016 / Jul. 10, 2018, James D. Rodgers.

(Continued)

*Primary Examiner* — Erich A Leeser
(74) *Attorney, Agent, or Firm* — Lathrop GPM LLP; Brian C. Trinque; Nicole Sassu

(57) ABSTRACT

Provided herein are compounds, pharmaceutical compositions comprising such compounds, and methods of using such compounds to treat diseases or disorders associated with JAK2 and/or ALK2.

12 Claims, 2 Drawing Sheets

(56) References Cited

U.S. PATENT DOCUMENTS

| | | | |
|---|---|---|---|
| 9,358,229 | B2 | 6/2016 | Vannucchi et al. |
| 9,359,358 | B2 | 6/2016 | Rodgers et al. |
| 9,487,521 | B2 | 11/2016 | Zhou et al. |
| 9,993,480 | B2 | 6/2018 | Vannucchi et al. |
| 10,166,191 | B2 | 1/2019 | Ni et al. |
| 10,196,392 | B2 | 2/2019 | Hopkins et al. |
| 10,710,980 | B2 | 7/2020 | Arista et al. |
| 2004/0009983 | A1 | 1/2004 | Cox et al. |
| 2004/0067985 | A1 | 4/2004 | Haviv et al. |
| 2004/0214928 | A1 | 10/2004 | Aronov et al. |
| 2005/0153989 | A1 | 7/2005 | Grotzfeld et al. |
| 2010/0113416 | A1 | 5/2010 | Friedman et al. |
| 2011/0207754 | A1 | 8/2011 | Li et al. |
| 2013/0137681 | A1 | 5/2013 | Rodgers et al. |
| 2015/0065447 | A1 | 3/2015 | Sandor |
| 2015/0250790 | A1 | 9/2015 | Parikh et al. |
| 2021/0393605 | A1 | 12/2021 | Séguy et al. |

FOREIGN PATENT DOCUMENTS

| | | | | |
|---|---|---|---|---|
| WO | WO 2001/42246 | * | 6/2001 | ........... C07D 487/04 |
| WO | WO 2001/042246 | | 6/2001 | |
| WO | WO 2002/000661 | | 1/2002 | |
| WO | WO 2003/004472 | A1 | 1/2003 | |
| WO | WO 2003/093297 | A2 | 11/2003 | |
| WO | WO 2004/000318 | A2 | 12/2003 | |
| WO | WO 2004/055009 | A1 | 7/2004 | |
| WO | WO 2004/092727 | A2 | 10/2004 | |
| WO | WO 2004/099204 | | 11/2004 | |
| WO | WO 2004/099205 | | 11/2004 | |
| WO | WO 2005/013986 | | 2/2005 | |
| WO | WO 2005/115985 | A1 | 12/2005 | |
| WO | WO 2006/025783 | A1 | 3/2006 | |
| WO | WO 2006/046024 | | 5/2006 | |
| WO | WO 2006/096270 | | 9/2006 | |
| WO | WO 2006/127587 | | 11/2006 | |
| WO | WO 2007/011760 | A2 | 1/2007 | |
| WO | WO 2007/084455 | A1 | 7/2007 | |
| WO | WO 2008/002671 | A2 | 1/2008 | |
| WO | WO 2010/008739 | A2 | 1/2010 | |
| WO | WO 2012/088438 | A1 | 6/2012 | |
| WO | WO 2012/161877 | A1 | 11/2012 | |
| WO | WO 2013/036869 | A2 | 3/2013 | |
| WO | WO 2014/138088 | A1 | 9/2014 | |
| WO | WO 2014/151871 | A2 | 9/2014 | |
| WO | WO 2015/061247 | A2 | 4/2015 | |
| WO | WO 2016/118638 | A1 | 7/2016 | |
| WO | WO 2018/014829 | A1 | 1/2018 | |
| WO | WO 2018/106820 | A1 | 6/2018 | |
| WO | WO 2020/041466 | | 2/2020 | |
| WO | WO 2021/062163 | | 4/2021 | |
| WO | WO 2021/062171 | | 4/2021 | |

OTHER PUBLICATIONS

U.S. Appl. No. 16/003,210 / 2019/0046534 / U.S. Pat. No. 10,610,530, Jun. 8, 2008 / Feb. 14, 2019 / Apr. 7, 2020, Hui-Yin Li.
U.S. Appl. No. 16/806,244 / 2020/0197401, Mar. 2, 2020 / Jun. 25, 2020, Hui-Yin Li.
U.S. Appl. No. 17/170,690 / 2021/0155606, Feb. 8, 2021 / May 27, 2021, Luca Arista.
U.S. Appl. No. 16/884,666 / 2020/0299265 / U.S. Pat. No. 10,947,218, May 27, 2020 / Sep. 24, 2020 / Mar. 16, 2021, Luca Arista.
U.S. Appl. No. 16/318,250 / 2019/0161474 / U.S. Pat. No. 10,710,980, Jan. 16, 2019 / May 30, 2019 / Jul. 14, 2020, Luca Arista.
U.S. Appl. No. 17/348,102 / 2021/0393605, Jun. 15, 2021 / Dec. 23, 2021, Francis Séguy.
U.S. Appl. No. 16/953,989 / 2021/015419, Feb. 26, 2021 / May 27, 2021, Yaoyu Chen.
International Preliminary Report on Patentability for International Application No. PCT/US2020/061497, dated May 17, 2022, 8 pages.
International Search Report and Written Opinion for International Application No. PCT/US2020/061497, dated Feb. 18, 2021, 11 pages.
Arber DA, Orazi A, Hasserjian R, et al. The 2016 revision to the World Health Organization classification of myeloid neoplasms and acute leukemia, Blood. 2016;127:2391-2405.
Greenberg PL, Tuechler H, Schanz J, et al. Revised International Prognostic Scoring System for Myelodysplastic Syndromes. Blood. 2012;120(12):2454-2465.
Passamonti F, and Maffioli M. Update from the latest WHO classification of MPNs: a user's manual. Hematology. 2016;9:534-542.
Barosi G, Mesa RA, Thièle J, et al. Proposed criteria for the diagnosis of post-polycythemia vera and post-essential thrombocythemia myelofibrosis: a consensus statement from the international working group for myelofibrosis research and treatment. Leukemia. 2008;22:437-438.
Gwaltney C, Paty J, Kwitkowskic VE, et al. Development of a harmonized patient-reported outcome questionnaire to assess myelofibrosis symptoms in clinical trials. Leuk Res. 2017;59:26-31.
Affidavit dated Jun. 4, 2010, submitted by proprietor during examination proceedings for U.S. Appl. No. 12/137,892.
Chapter 4 of "Process Chemistry in the Pharmaceutical Industry, vol. 2 Challenges in an Ever Changing Climate," 2007.
Berge et al., "Pharmaceutical salts" Journal of Pharmaceutical Science, vol. 66 No. 1 Jan. 1977, pp. 1-19.
Gould, P.S. "Salt selection for basic drugs" published in Int J Pharmaceutics 1986, 33, 201-217.
Black, S.N., et al., "Structure Solubility, Screening and Synthesis of Molecular Salts" published in J Pharm Sci May 2007, 96, 1053-1068.
Steffen Paulekuhn, G., et al., "Trends in active pharmaceutical ingredient salt selection based on analysis of orange book database" published in J. Med. Chem., Dec. 2007, 50, 6665-6672.
Bastin, R. J. et al., Salt selection and optimization procedures for pharmaceutical new chemical entitles published in Organic Process Research & Development 2000, 4n 427-435 3 Sep. 6, 2019.
Quintas-Cardarna, A., et al., Preclinical characterization of the selective JAK1/2 inhibitor INCB018424: therapeutic implications for the treatment of myeloproliferative neoplasms published in Blood 2010, 115, 3109-3117.
Levine, et al., Cancer Cell, vol. 7, 2005: 387-397.
Open Label Ruxolitinib (INB018424) in Patients with Myelofibrosis and Post Polycythemia Ver/Essential Thrombocythemia Myelofibrosis; start date Jun. 2007.
Baxter et al. "Acquired mutation of the tyrosine kinase JAK2 in human myeloproliferative disorders" The Lancet (2005), 365: 1054-1061.
Wernig et al. "Efficacy of TG101348, a selective JAK2 inhibitor, in Treatment of a Murine Model of JAK2V617F-Induced Polycythemia Vera." Cancer Cell (2008), 13: 311-320.
Gura, Science Nov. 7, 1997: vol. 278 No. 5340, pp. 1041-1042.
Roberts, Jr et al., JAMA 292 (17): 2130-2140 (2004).
Kamb, Nature Reviews Drug Discovery 4, pp. 161-165 (Feb. 2005).
Kola, Nature Reviews Drug Discovery 3, pp. 711-715 (2004).
"Expert Scientific Group on Phase one Clinical Trials Final Report" Nov. 30, 2006, pp. C1, C35-C38.
ClinicalTrials.gov https://clinicaltrials.gov/ct2/show/NCT00227591 downloaded Jan. 7, 2021.
"Remington's pharmaceutical sciences," 17th ed., 1985, Mack Publishing Co., Easton, PA.
Asshoff et al., "Momelotinib inhibits ACVR1/ALK2, decreases hepcidin production, and ameliorates anemia of chronic disease in rodents." Blood, Mar. 30, 2017, 129(13), pp. 1823-1830.
Bose et al., "Management of Myelofibrosis-Related Cytopenias." Curr Hematol Malig Rep., 2018, 13(3), pp. 164-172.
Bose et al., "Myelofibrosis: an update on drug therapy in 2016." Expert Opin Pharmacother., 2016, 17(18) pp. 2375-2389.
Gerds et al., "A Phase 2 Study of Luspatercept in Patients with Myelofibrosis-Associated Anemia" ASH Annual Meeting, Dec. 9, 2019, 6 pages.
Hopkins, "Inhibitors of the bone morphogenetic protein (BMP) signaling pathway: a patent review." Expert opinion on therapeutic patents., 2016, 26(10), pp. 1115-1128.

(56) References Cited

OTHER PUBLICATIONS

Kim et al., "Identification of novel ALK2 inhibitors and their effect on cancer cells", Biochemical and Biophysical Research Communications, 2017, 492, pp. 121-127.
Mohedas et al., "Development of an ALK2-biased BMP type I receptor kinase inhibitor", ACS Chemical Biology, Jun. 21, 2013, 8(6): 1291-1302.
Mohedas et al., "Structure-Activity Relationship of 3,5-Diaryl-2-aminopyridine ALK2 Inhibitors Reveals Unaltered Binding Affinity for Fibrodysplasia Ossificans Progressiva Causing Mutants", Journal of Medicinal Chemistry, Aug. 7, 2014, 57(19): 7900-7915.
Notification of Transmittal of The International Search Report and The Written Opinion of the International Searching Authority, or the Declaration, dated Oct. 24, 2017 in International Application No. PCT/CN2017/093385, International Filing Date: Jul. 18, 2017.
Written Opinion of the International Searching Authority, dated Dec. 13, 2009 in International Application No. PCT/US2008/066662, 6 pages.

\* cited by examiner

COMBINATION THERAPY COMPRISING AN ALK2 INHIBITOR AND A JAK2 INHIBITOR

RELATED APPLICATIONS

This application claims priority to U.S. Provisional Application No. 62/939,241 filed on Nov. 22, 2019, U.S. Provisional Application No. 62/980,562 filed on Feb. 24, 2020, U.S. Provisional Application No. 63/035,194 filed on Jun. 5, 2020, and U.S. Provisional Application No. 63/056,768 filed on Jul. 27, 2020, the contents of which are hereby incorporated in their entireties.

BACKGROUND

Myeloproliferative neoplasms (MPNs) are a group of disorders that cause an overproduction of blood cells (platelets, white blood cells and red blood cells) in the bone marrow. MPNs include polycythemia vera (PV), primary or essential thrombocythemia (ET), primary or idiopathic myelofibrosis, chronic myelogenous (myelocytic) leukemia (CML), chronic neutrophilic leukemia (CNL), juvenile myelomonocytic leukemia (JML) and chronic eosinophilic leukemia (CEL)/hyper eosinophilic syndrome (HES). These disorders are grouped together because they share some or all of the following features: involvement of a multipotent hematopoietic progenitor cell, dominance of the transformed clone over the non-transformed hematopoietic progenitor cells, overproduction of one or more hematopoietic lineages in the absence of a definable stimulus, growth factor-independent colony formation in vitro, marrow hypercellularity, megakaryocyte hyperplasia and dysplasia, abnormalities predominantly involving chromosomes 1, 8, 9, 13, and 20, thrombotic and hemorrhagic diatheses, exuberant extramedullary hematopoiesis, and spontaneous transformation to acute leukemia or development of marrow fibrosis but at a low rate, as compared to the rate in CML. The incidence of MPNs varies widely, ranging from approximately 3 per 100,000 individuals older than 60 years annually for CML to 0.13 per 100,000 children from birth to 14 years annually for JML (Vardiman J W et al., Blood 100 (7): 2292-302, 2002).

There remains a need for new treatments of MPNs, as well as other cancers and related indications.

SUMMARY

Provided herein is a combination therapy comprising an ALK2 inhibitor and a JAK2 inhibitor. The combination therapy is useful for the treatment of a variety of cancers, including MPNs, and related indications, such as anemia. The combination therapy is also useful for the treatment of any number of JAK2-associated and/or ALK2-associated diseases.

In an aspect, provided herein is a pharmaceutical combination comprising a JAK2 inhibitor, or pharmaceutically acceptable salt thereof, and an ALK2 inhibitor, or a pharmaceutically acceptable salt thereof.

In another aspect, provided herein is a pharmaceutical combination comprising (i) a JAK2 inhibitor having the Formula I:

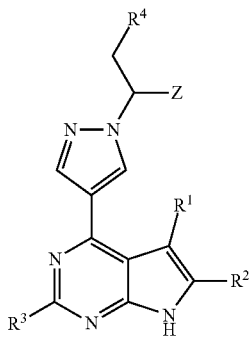

or a pharmaceutically acceptable salt thereof; and
(ii) an ALK2 inhibitor having the Formula II:

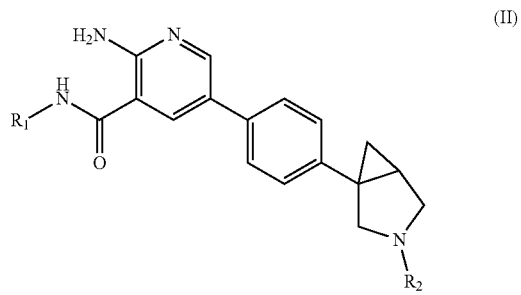

or a pharmaceutically acceptable salt thereof.

In yet another aspect, provided herein is a pharmaceutical composition comprising an ALK2 inhibitor, or pharmaceutically acceptable salt thereof, a JAK2 inhibitor, or pharmaceutically acceptable salt thereof, and a pharmaceutically acceptable carrier.

In still another aspect, provided herein is a pharmaceutical composition comprising an ALK2 inhibitor, a pharmaceutically acceptable carrier, and a JAK2 inhibitor having the Formula I:

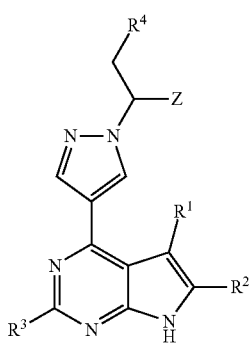

or a pharmaceutically acceptable salt thereof.

In an embodiment of the pharmaceutical composition, the ALK2 inhibitor is a compound of Formula II:

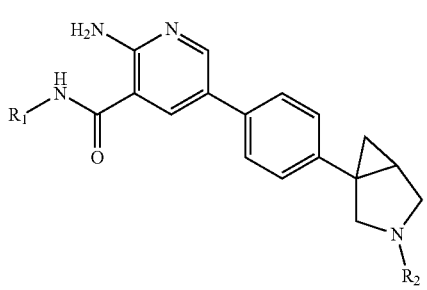

(II)

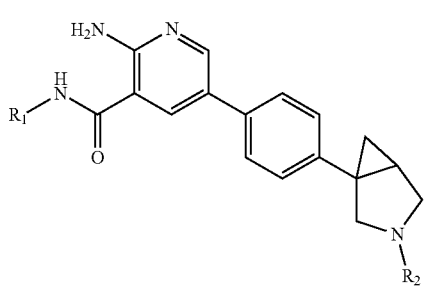

(II)

or a pharmaceutically acceptable salt thereof.

In yet another aspect, provided herein is a method of treating cancer in a subject in need thereof, comprising administering to the subject an ALK2 inhibitor, or pharmaceutically acceptable salt thereof, and a JAK2 inhibitor, or pharmaceutically acceptable salt thereof.

In still another aspect, provided herein is a method of treating cancer in a subject in need thereof, comprising administering to the subject an ALK2 inhibitor, or pharmaceutically acceptable salt thereof, and a JAK2 inhibitor having the Formula I:

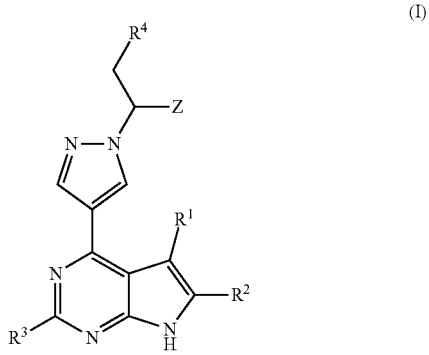

(I)

or a pharmaceutically acceptable salt thereof.

In an embodiment of the methods, the ALK2 inhibitor is a compound of Formula II:

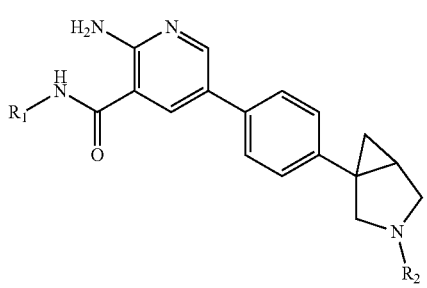

(II)

or a pharmaceutically acceptable salt thereof.

In an aspect, provided herein is a method of treating cancer in a subject in need thereof, comprising administering to the subject an ALK2 inhibitor, or pharmaceutically acceptable salt thereof.

In an embodiment of the method of treating cancer, the ALK2 inhibitor is a compound of Formula II:

or a pharmaceutically acceptable salt thereof.

In another embodiment of the method of treating cancer, the ALK2 inhibitor is administered as a monotherapy. In yet another embodiment, the ALK2 inhibitor is administered in the absence of any other active pharmaceutical ingredient. In still another embodiment, the ALK2 inhibitor is administered in the absence of a JAK2 inhibitor.

DETAILED DESCRIPTION

Figure 1:
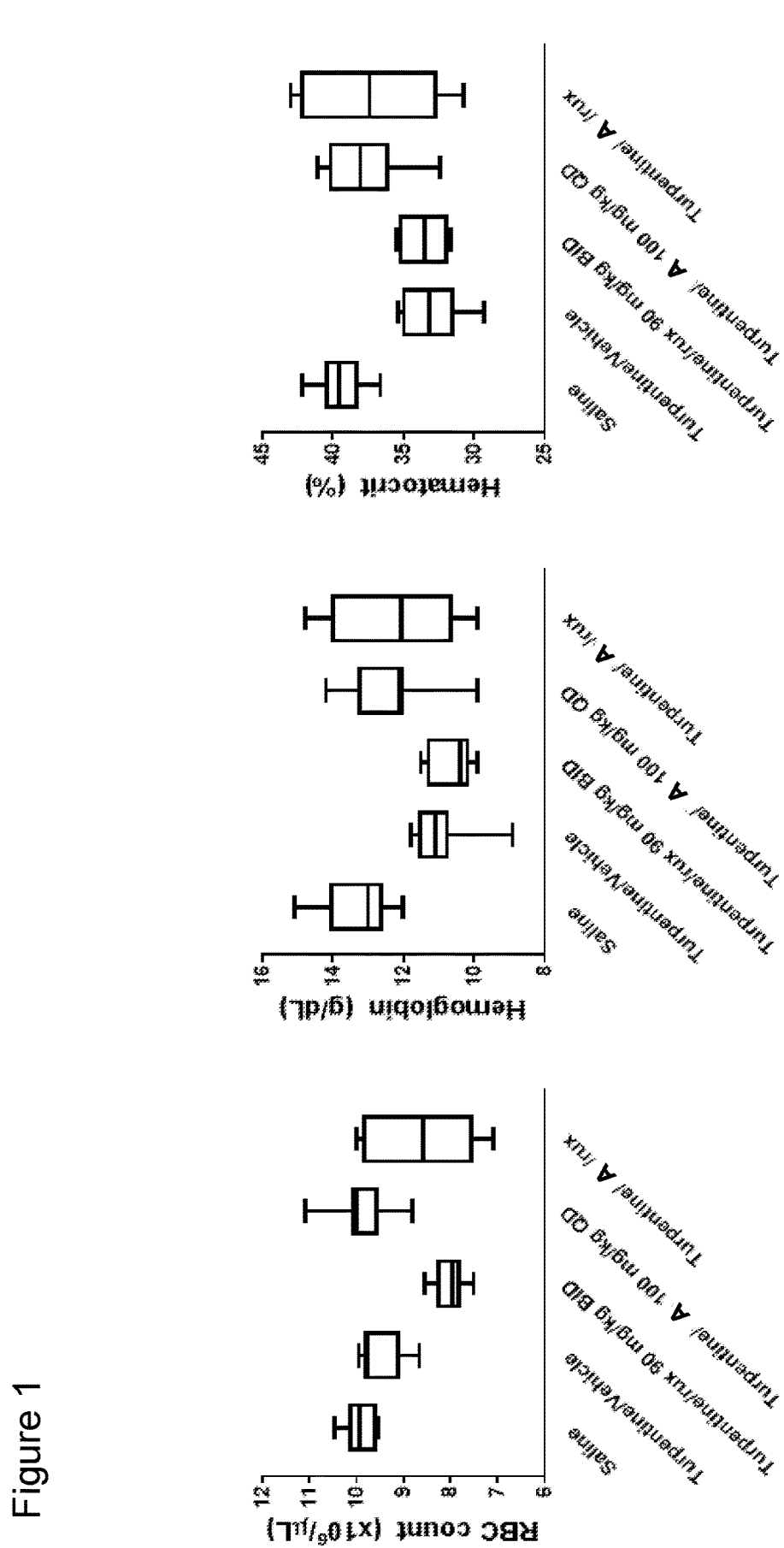
FIG. 1 shows how 100 mg/kg QD of a Compound of Formula II corrects anemia in mice brought on by turpentine alone, or in combination with a Compound of Formula I.

Administering a combination of an ALK2 inhibitor and a JAK2 kinase inhibitor provides surprising, synergistic effects for treating cancer, e.g., myeloproliferative neoplasms (MPNs), in a subject. Such an approach—combination or co-administration of the two types of agents—can be useful for treating individuals suffering from cancer who, for example, do not respond to or are resistant to currently available therapies.

As described herein, low doses of the ALK2 inhibitor and JAK2 inhibitor may be used effectively to treat cancer, thus providing at least one basis that there is synergy in administering the combination of agents that may permit lower dosing of each agent (relative to presently approved, recommended doses used by clinicians) to get effective treatment. This provides potentially dramatic tolerability and efficacy advantages over other anti-cancer agents.

Also described herein are methods of treating cancers using the ALK2 inhibitor as a monotherapy, e.g., in the absence of a JAK2 inhibitor.

Certain terms used herein are described below. Compounds of the present disclosure are described using standard nomenclature. Unless defined otherwise, all technical and scientific terms used herein have the same meaning as is commonly understood by one of skill in the art to which this invention belongs.

Definitions

Listed below are definitions of various terms used herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, "pharmaceutical combination" or "combination" refers to formulations of the separate compounds with or without instructions for combined use or to combination products. The combination compounds may thus be entirely separate pharmaceutical dosage forms or in pharmaceutical compositions that are also sold independently of each other and where just instructions for their combined use are provided in the package equipment, e.g., leaflet or the like, or in other information, e.g., provided to physicians and medical staff (e.g. oral communications, communications in writing or the like), for simultaneous or sequential use for being jointly active.

As used herein, the term "monotherapy" means that the treatment uses a single active pharmaceutical ingredient to treat a disease or condition. A monotherapy can still include treatment with a pharmaceutically acceptable carrier or excipient. In an embodiment of the methods provided herein, the single active pharmaceutical ingredient is a compound of Formula II. In another embodiment, a compound of Formula II is administered as a monotherapy not in conjunction with a Janus kinase inhibitor.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease. In some embodiments, the term "treating" or "treatment" refers to inhibiting or ameliorating the disease.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein a parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts described herein include the conventional non-toxic salts of the parent compound formed, for example, from non-toxic inorganic or organic acids. The pharmaceutically acceptable salts discussed herein can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound with a pharmaceutically acceptable carrier. The pharmaceutical composition facilitates administration of the composition to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound disclosed herein, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of a compound disclosed herein, and are physiologically acceptable to the patient. Supplementary active compounds may also be incorporated into the compositions. The "pharmaceutically acceptable carrier" may further include a pharmaceutically acceptable salt of the compound(s) disclosed herein. Other additional ingredients that may be included in the pharmaceutical compositions are known in the art and described, for example, in Remington's Pharmaceutical Sciences (Genaro, Ed., Mack Publishing Co., 1985, Easton, Pa.), which is incorporated herein by reference.

As used herein, the term "ALK2" or "ALK-2" refers to activin A receptor, type I (ACVRI), also known as ACVRLK2; SKR1; ACVR1A; Activin receptor type I; Activin receptor-like kinase 2; Serine/threonine-protein kinase receptor R1; TGF-B superfamily receptor type I; ACTRI; TSRI; activin A receptor, type II-like kinase 2; activin receptor type-1; hydroxyalkyl-protein kinase; ACTR-I; TSR-I. Therefore, an "ALK2 inhibitor," as used herein, refers to a compound that modulates the activity of ALK2.

As used herein, the term "JAK2" refers to Janus kinase-2, a member of the Janus family of intracellular, nonreceptor tyrosine kinases (JAK1, JAK2, JAK3, TYK2) that transduce cytokine-mediated signals via the JAK-STAT pathway. Therefore, a "JAK2 inhibitor," as used herein, refers to a compound that modulates the activity of JAK2. A JAK2 inhibitor includes compounds that specifically modulate JAK2 as well as compounds that modulate JAK2 and one or more other Janus kinases, e.g., JAK1/2 inhibitor compounds.

The term "single formulation" as used herein refers to a single carrier or vehicle formulated to deliver effective amounts of both therapeutic agents to a patient. The single vehicle is designed to deliver an effective amount of each of the agents, along with any pharmaceutically acceptable carriers or excipients. In some embodiments, the vehicle is a tablet, capsule, pill, or a patch. In other embodiments, the vehicle is a solution or a suspension.

The term "unit dose" is used herein to mean simultaneous administration of both agents together, in one dosage form, to the patient being treated. In some embodiments, the unit dose is a single formulation. In certain embodiments, the unit dose includes one or more vehicles such that each vehicle includes an effective amount of at least one of the agents along with pharmaceutically acceptable carriers and excipients. In some embodiments, the unit dose is one or more tablets, capsules, pills, or patches administered to the patient at the same time.

The term "combination therapy" refers to the administration of two or more therapeutic compounds to treat a therapeutic condition or disorder described in the present disclosure. Such administration encompasses co-administration of these therapeutic compounds in a substantially simultaneous manner, such as in a single capsule having a fixed ratio of active ingredients or in multiple, or in separate containers (e.g., capsules) for each active ingredient. In addition, such administration also encompasses use of each type of therapeutic compound in a sequential manner, either at approximately the same time or at different times. In either case, the treatment regimen will provide beneficial effects of the drug combination in treating the conditions or disorders described herein.

The combination of agents described herein may display a synergistic effect. The term "synergistic effect" as used herein, refers to action of two agents such as, for example, an ALK2 inhibitor (e.g., an ALK2 inhibitor of formula II) and a JAK2 inhibitor (e.g., a JAK2 inhibitor of formula I), producing an effect, for example, slowing the symptomatic progression of cancer or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

As used herein, the term "synergy" refers to the effect achieved when the active ingredients, i.e., ALK2 inhibitor and JAK2 inhibitor, used together is greater than the sum of the effects that results from using the compounds separately.

In an embodiment, provided herein is a combination therapy comprising an effective amount of a JAK2 inhibitor and an ALK2 inhibitor. An "effective amount" of a combination of agents (i.e., an ALK2 inhibitor (e.g., an ALK2 inhibitor of formula II) and a JAK2 inhibitor (e.g., a JAK2 inhibitor of formula I)) is an amount sufficient to provide an observable improvement over the baseline clinically observable signs and symptoms of the disorders treated with the combination.

An "oral dosage form" includes a unit dosage form prescribed or intended for oral administration.

Provided herein is a combination of therapeutic agents and administration of the combination of agents to treat cancer, and related indications. As used herein, the term "cancer" includes related indications, such as anemia. As used herein, a "combination of agents" and similar terms refer to a combination of two types of agents: an ALK2 inhibitor, or a pharmaceutically acceptable salt thereof, and a JAK2 inhibitor, or a pharmaceutically acceptable salt thereof. Use of racemic mixtures of the individual agents is also provided. Pharmacologically active metabolites include those that are inactive but converted into pharmacologically active forms in the body after administration.

As used herein, the term "alkyl," by itself or as part of another substituent means, unless otherwise stated, a straight or branched chain hydrocarbon having the number of carbon atoms designated (i.e., $C_1$-$C_6$-alkyl means an alkyl having one to six carbon atoms) and includes straight and branched chains. In an embodiment, $C_1$-$C_3$, $C_1$-$C_4$, $C_1$-$C_6$ alkyl groups are provided herein. Examples include methyl, ethyl, propyl, isopropyl, butyl, isobutyl, tert-butyl, pentyl, neopentyl, and hexyl.

As used herein, the term "alkenyl" refers to a monovalent group derived from a hydrocarbon moiety containing, in certain embodiments, from two to four, two to six, or two to eight carbon atoms having at least one carbon-carbon double bond. The alkenyl group may or may not be the point of attachment to another group. The term "alkenyl" includes, but is not limited to, ethenyl, 1-propenyl, 1-butenyl, heptenyl, octenyl and the like.

As used herein, the term "alkynyl" refers to a monovalent group derived from a hydrocarbon moiety containing, in certain embodiments, from two to four, two to six, or two to eight carbon atoms having at least one carbon-carbon triple bond. The alkynyl group may or may not be the point of attachment to another group. The term "alkynyl" includes, but is not limited to, ethynyl, 1-propynyl, 1-butynyl, heptynyl, octynyl and the like.

As used herein, the term "alkoxy," refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like. In an embodiment, $C_1$-$C_3$, $C_1$-$C_4$, $C_1$-$C_6$ alkoxy groups are provided herein.

As used herein, the term "halo" or "halogen" alone or as part of another substituent means, unless otherwise stated, a fluorine, chlorine, bromine, or iodine atom.

As used herein, the term "cycloalkyl" means a non-aromatic carbocyclic system that is partially or fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-10, 3-8, 3-7, 3-6, and 5-10 atoms. The term "cycloalkyl" includes, but is not limited to, cyclopropyl, cyclobutyl, cyclopentyl, cyclohexyl, bicyclo[3.1.0]hexyl, spiro[3.3]heptanyl, bicyclo[2.2.2]octanyl and bicyclo[1.1.1] pentyl. In an embodiment, 3-10 membered cycloalkyl groups are provided herein. In another embodiment, Ca cycloalkyl groups are provided herein. In yet another embodiment, bicyclo-C cycloalkyl groups are provided herein.

As used herein, the term "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocycloalkyl also includes bicyclic structures that may be bridged or spirocyclic in nature with each individual ring within the bicycle varying from 3-8, 5-10, 4-6, or 3-10 atoms, and containing 0, 1, or 2 N, O, or S atoms. The term "heterocycloalkyl" includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-aza-bicyclo[2.1.1]hexanyl, 5-azabicyclo[2.1.1]hexanyl, 6-azabicyclo[3.1.1] heptanyl, 2-azabicyclo-[2.2.1]heptanyl, 3-aza-bicyclo[3.1.1]heptanyl, 2-azabicyclo[3.1.1]heptanyl, 3-azabicyclo-[3.1.0] hexanyl, 2-aza-bicyclo[3.1.0]hexanyl, 3-azabicyclo[3.2.1] octanyl, 8-azabicyclo[3.2.1]-octanyl, 3-oxa-7-aza-bicyclo [3.3.1]nonanyl, 3-oxa-9-azabicyclo[3.3.1]nonanyl, 2-oxa-5-aza-bicyclo[2.2.1]heptanyl, 6-oxa-3-azabicyclo[3.1.1] heptanyl, 2-azaspiro[3.3]heptanyl, 2-oxa-6-azaspiro[3.3] heptanyl, 2-oxaspiro[3.3]heptanyl, 2-oxaspiro[3.5]nonanyl, 3-oxaspiro[5.3]-nonanyl, and 8-oxabicyclo-[3.2.1]octanyl. In an embodiment, 3-10 membered heterocycloalkyl groups are provided herein. In another embodiment, 5-10 membered heterocycloalkyl groups are provided herein. In still another embodiment, 4-6 membered heterocycloalkyl groups are provided herein.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. The term "heteroaryl" includes, but is not limited to, furanyl, thiophenyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]-pyridinyl, pyrazolo [1,5-a]pyridinyl, 5,6,7,8-tetrahydroisoquinolinyl, 5,6,7,8-tetra-hydroquinolinyl, 6,7-dihydro-5H-cyclopenta[b]pyridinyl, 6,7-dihydro-5H-cyclopenta[c]-pyridinyl, 1,4,5,6-tetrahydrocyclopenta[c]pyrazolyl, 2,4,5,6-tetrahydrocyclopenta[c]-pyrazolyl, 5,6-dihydro-4H-pyrrolo [1,2-b]pyrazolyl, 6,7-dihydro-5H-pyrrolo[1,2-b]-[1,2,4] triazolyl, 5,6,7,8-tetrahydro-[1,2,4]triazolo[1,5-a]pyridinyl, 4,5,6,7-tetrahydro-pyrazolo[1,5-a]pyridinyl, 4,5,6,7-tetrahydro-1H-indazolyl and 4,5,6,7-tetrahydro-2H-indazolyl. In an embodiment, 5-10 membered heteroaryl groups are provided herein.

It is to be understood that if a cycloalkyl, heterocycloalkyl, or heteroaryl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thienyl" means 2- or 3-thioenyl, and so forth.

As used herein, the term "substituted" means that an atom or group of atoms has replaced hydrogen as the substituent attached to another group.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

Pharmaceutical Combinations

In an aspect, provided herein is a pharmaceutical combination comprising a JAK2 inhibitor, or pharmaceutically acceptable salt thereof, and an ALK2 inhibitor, or a pharmaceutically acceptable salt thereof.

In another aspect, provided herein is a pharmaceutical combination comprising an ALK2 inhibitor, or a pharmaceutically acceptable salt thereof, and (i) a JAK2 inhibitor having the Formula I:

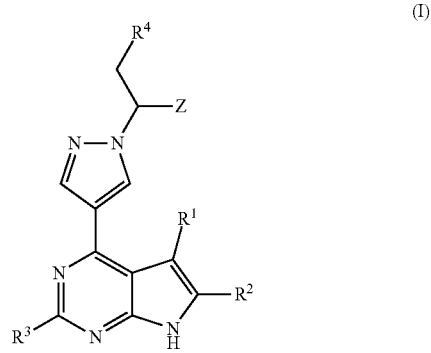

(I)

or a pharmaceutically acceptable salt thereof;

wherein

R¹, R² and R³ are independently selected from the group consisting of hydrogen, halo, and $C_{1-4}$ alkyl;

R⁴ is selected from the group consisting of hydrogen, halo, cyano, nitro, hydroxy, $C_{1-4}$ alkyl, and $C_{1-4}$ alkoxy; and Z is 3-6 membered cycloalkyl.

In an embodiment of the pharmaceutical combinations, the ALK2 inhibitor is a compound of Formula II:

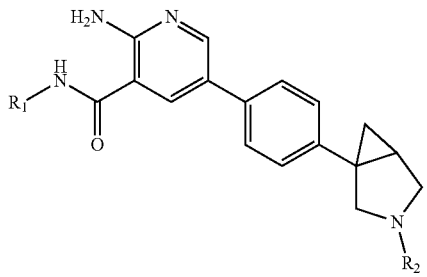

(II)

or a pharmaceutically acceptable salt thereof;
wherein $R_1$ is bridged 5-10 membered cycloalkyl optionally substituted one, two, or three times with hydroxyl or $C_1$-$C_3$ alkoxy;

$R_2$ is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with $R_3$; and $R_3$ is selected from the group consisting of hydroxy, halo, cyano, nitro, $SO_2$—$C_1$-$C_3$ alkyl, and $SO_3H$.

In an embodiment of Formula II, $R_1$ is bridged C-cycloalkyl substituted with hydroxyl. In another embodiment, $R_2$ is tetrahydropyran. In yet another embodiment, $R_1$ is bridged $C_8$-cycloalkyl substituted with hydroxyl and $R_2$ is tetrahydropyran.

In yet another aspect, provided herein is a pharmaceutical combination comprising (i) a JAK2 inhibitor having the Formula I:

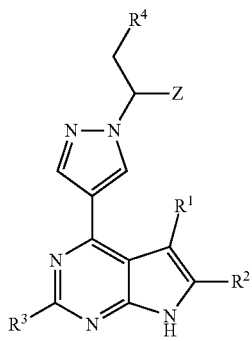

(I)

or a pharmaceutically acceptable salt thereof;
wherein

R¹, R² and R³ are independently selected from the group consisting of hydrogen, halo, and $C_{1-4}$ alkyl;

R⁴ is selected from the group consisting of hydrogen, halo, cyano, nitro, hydroxy, $C_{1-4}$ alkyl, and $C_{1-4}$ alkoxy;

Z is 3-6 membered cycloalkyl; and (ii) an ALK2 inhibitor having the Formula IIa:

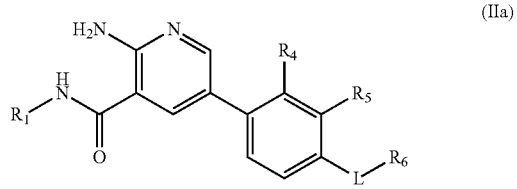

(IIa)

or a pharmaceutically acceptable salt thereof;
wherein

L is a bond, $(CH_2)_n$, —CH(CH₃)—, —O—$(CH_2)_n$—, —C(O)—, or —C(O)—NH—$(CH_2)_n$—;

n is 1, 2, or 3;

$R_1$ is selected from 3-7 membered cycloalkyl optionally substituted one, two, or three times with a substituent independently selected from hydroxyl, halogen, $C_1$-$C_3$ alkyl; bridged 5-10 membered cycloalkyl optionally substituted one, two, or three times with hydroxyl or $C_1$-$C_3$ alkoxy;

$R_4$ and $R_5$ are each independently selected from the group consisting of H, halogen, $C_1$-$C_3$ alkyl;

$R_6$ is 5-10 membered heterocycloalkyl optionally substituted one, two, or three times with $R_2$;

$R_2$ is independently, at each occurrence, selected from the group consisting of $C_1$-$C_3$ alkyl, $C_1$-$C_3$ alkoxy, $C_1$-$C_3$ alkoxy-$C_1$-$C_3$ alkyl, $C_1$-$C_3$ alkyl, $C_2$-$C_4$ alkynyl, $C_1$-$C_3$ alkyl, $(CH_2)_m$—$R_3$, wherein alkyl and alkoxy are optionally substituted one, two, or three times independently with halo or cyano;

m is 0, 1, 2 or 3;

$R_3$ is 4-6 membered heterocycloalkyl optionally substituted one, two, or three times with a substituent independently selected from the group consisting of oxo, $SO_2$—$C_1$-$C_3$ alkyl, $C_1$-$C_3$ alkyl, and 3-6 membered cycloalkyl, wherein alkyl and cycloalkyl are optionally substituted one, two, or three times with halo;

alternatively, two $R_3$, together with the atoms to which they are attached, form a 3-6 membered cycloalkyl.

In an embodiment of Formula IIa, L-$R_6$ is

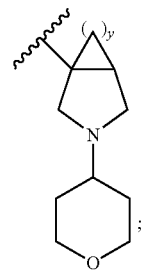

wherein y is 1, 2, or 3.

In an embodiment of the pharmaceutical combinations, the ALK2 inhibitor of Formula IIa is a compound of Formula IIb:

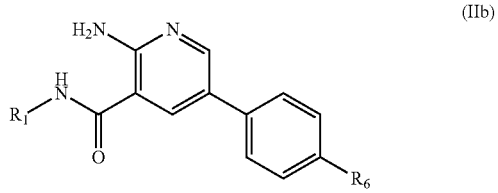

(IIb)

or a pharmaceutically acceptable salt thereof.

In yet another aspect, provided herein is a pharmaceutical combination comprising (i) a JAK2 inhibitor having the Formula I:

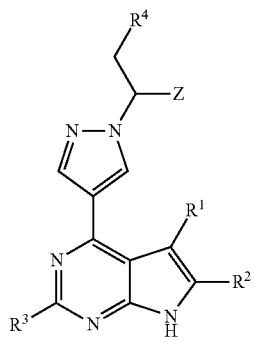

(I)

or a pharmaceutically acceptable salt thereof;
wherein $R^1$, $R^2$ and $R^3$ are independently selected from the group consisting of hydrogen, halo, and $C_{1-4}$ alkyl;

$R^4$ is selected from the group consisting of hydrogen, halo, cyano, nitro, hydroxy, $C_{1-4}$ alkyl, and $C_{1-4}$ alkoxy;

Z is 3-6 membered cycloalkyl; and (ii) an ALK2 inhibitor having the Formula II:

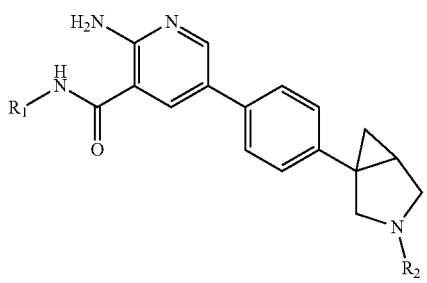

(II)

or a pharmaceutically acceptable salt thereof;
wherein $R_1$ is bridged 5-10 membered cycloalkyl optionally substituted one, two, or three times with hydroxyl or $C_1$-$C_3$ alkoxy;

$R_2$ is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with $R^3$; and $R^3$ is selected from the group consisting of hydroxy, halo, cyano, nitro, $SO_2$—$C_1$-$C_3$ alkyl, and $SO_3H$.

In an embodiment of Formula I, $R^1$ is hydrogen. In another embodiment, $R^2$ is hydrogen. In yet another embodiment, $R^3$ is hydrogen. In still another embodiment, $R^4$ is cyano. In an embodiment, $R^1$, $R^2$ and $R^3$ are all hydrogen, and $R^4$ is cyano. In another embodiment, Z is cyclopentyl.

In an embodiment of Formula II, $R_1$ is bridged Ca-cycloalkyl substituted with hydroxyl. In another embodiment, $R_1$ is

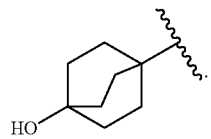

In yet another embodiment, $R_2$ is tetrahydropyran. In another embodiment, $R_1$ is bridged Ca-cycloalkyl substituted with hydroxyl and $R_2$ is tetrahydropyran.

In an embodiment of Formula II, L-$R_6$ is

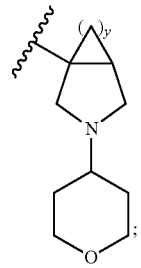

wherein y is 1, 2, or 3.

In another embodiment of the pharmaceutical combinations, the JAK2 inhibitor of Formula I is 3-cyclopentyl-3-[4-(7H-pyrrolo[2,3-d]pyrimidin-4-yl)-1H-pyrazol-1-yl]-propanenitrile, or a pharmaceutically acceptable salt thereof.

In yet another embodiment of the pharmaceutical combinations, the JAK2 inhibitor of Formula I is (3R)-3-cyclopentyl-3-[4-(7H-pyrrolo[2,3-d]pyrimidin-4-yl)-1H-pyrazol-1-yl]-propanenitrile, or a pharmaceutically acceptable salt thereof.

In another embodiment of the pharmaceutical combinations, the JAK2 inhibitor of Formula I is (3R)-3-cyclopentyl-3-[4-(7H-pyrrolo[2,3-d]pyrimidin-4-yl)-1H-pyrazol-1-yl]-propanenitrile phosphoric acid salt.

In still another embodiment of the pharmaceutical combinations, the ALK2 inhibitor of Formula II is 2-amino-N-(4-hydroxy-bicyclo[2.2.2]octan-1-yl)-5-(4-(3-(tetrahydro-2H-pyran-4-yl)-3-aza-bicyclo[3.1.0]hexan-1-yl)phenyl) nicotinamide, or a pharmaceutically acceptable salt thereof.

In an embodiment of the pharmaceutical combinations, the ALK2 inhibitor of Formula II is 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)nicotinamide (Compound A), or a pharmaceutically acceptable salt thereof.

In another embodiment of the pharmaceutical combinations, the ALK2 inhibitor of Formula II is 2-amino-N-(4-hydroxybicyclo-[2.2.2]octan-1-yl)-5-(4-((1S,5R)-3-(tetrahydro-2H-pyran-4-yl)-3-azabicyclo-[3.1.0]hexan-1-yl) phenyl)nicotinamide, or a pharmaceutically acceptable salt thereof.

In yet another embodiment of the pharmaceutical combinations, the JAK2 inhibitor of Formula I is 3-cyclopentyl-3-[4-(7H-pyrrolo[2,3-d]pyrimidin-4-yl)-1H-pyrazol-1-yl] propane-nitrile, or a pharmaceutically acceptable salt thereof, and the ALK2 inhibitor of Formula II is 2-amino-N-(4-hydroxybicyclo-[2.2.2]octan-1-yl)-5-(4-(3-(tetrahydro-2H-pyran-4-yl)-3-azabicyclo-[3.1.0]hexan-1-yl)phenyl)nicotinamide, or a pharmaceutically acceptable salt thereof.

In still another embodiment of the pharmaceutical combinations, the JAK2 inhibitor of Formula I is 3-cyclopentyl-3-[4-(7H-pyrrolo[2,3-d]pyrimidin-4-yl)-1H-pyrazol-1-yl] propane-nitrile phosphoric acid salt, and the ALK2 inhibitor of Formula II is 2-amino-N-(4-hydroxybicyclo-[2.2.2]octan-1-yl)-5-(4-(3-(tetrahydro-2H-pyran-4-yl)-3-azabicyclo-[3.1.0]hexan-1-yl)phenyl)-nicotinamide, or a pharmaceutically acceptable salt thereof.

In an embodiment of the pharmaceutical combinations, the JAK2 inhibitor of Formula I is (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, and the ALK2 inhibitor of Formula II is 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)nicotinamide (Compound A), or a pharmaceutically acceptable salt thereof.

In another embodiment of the pharmaceutical combinations, the JAK2 inhibitor of Formula I is (3R)-3-cyclopentyl-3-[4-(7H-pyrrolo[2,3-d]pyrimidin-4-yl)-1H-pyrazol-1-yl]propanenitrile phosphoric acid salt, and the ALK2 inhibitor of Formula II is 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)nicotinamide (Compound A), or a pharmaceutically acceptable salt thereof.

In an embodiment, the ALK2 inhibitor is administered at a dose selected from the group consisting of 5 mg, 10 mg, 15 mg, 20 mg, 25 mg, and 50 mg, In another embodiment, the ALK2 inhibitor is administered at a dose of 5 mg. In yet another embodiment, the ALK2 inhibitor is administered at a dose of 10 mg. In still another embodiment, the ALK2 inhibitor is administered at a dose of 15 mg. In an embodiment, the ALK2 inhibitor is administered at a dose of 20 mg. In another embodiment, the ALK2 inhibitor is administered at a dose of 25 mg. In yet another embodiment, the ALK2 inhibitor is administered at a dose of 50 mg. In still another embodiment, the ALK2 inhibitor is orally administered as a tablet. In another embodiment, the ALK2 inhibitor is administered once daily (QD)

In an embodiment, the JAK2 inhibitor is administered at a dose selected from the group consisting of 5 mg, 10 mg, 15 mg, 20 mg, 25 mg, and 50 mg, In another embodiment, the JAK2 inhibitor is administered at a dose of 5 mg. In yet another embodiment, the JAK2 inhibitor is administered at a dose of 10 mg. In still another embodiment, the JAK2 inhibitor is administered at a dose of 15 mg. In an embodiment, the JAK2 inhibitor is administered at a dose of 20 mg. In another embodiment, the JAK2 inhibitor is administered at a dose of 25 mg. In yet another embodiment, the JAK2 inhibitor is administered at a dose of 50 mg. In still another embodiment, the JAK2 inhibitor is orally administered as a tablet. In another embodiment, the JAK2 inhibitor is administered twice daily (BID).

In an embodiment, the ALK2 is administered at a dose of 50 mg QD, and the JAK2 inhibitor is administered at a dose of 15 mg BID. In another embodiment, the ALK2 is administered at a dose of 50 mg QD, and the JAK2 inhibitor is administered at a dose of 20 mg BID. In yet another embodiment, the ALK2 is administered at a dose of 50 mg QD, and the JAK2 inhibitor is administered at a dose of 25 mg BID. In still another embodiment, the ALK2 is administered at a dose of 50 mg QD, and the JAK2 inhibitor is administered at a dose of 10 mg BID.

The administration of a pharmaceutical combination provided herein may result in a beneficial effect, e.g. a synergistic therapeutic effect, e.g., with regard to alleviating, delaying progression of or inhibiting the symptoms, and may also result in further surprising beneficial effects, e.g., fewer side-effects, an improved quality of life or a decreased morbidity, compared with a monotherapy applying only one of the pharmaceutically active ingredients used in the combination of the invention.

The JAK2 inhibitors provided herein, their syntheses, and their biological activity against JAK2 can be found in PCT/US2006/047369 (WO2007070514), which is incorporated by reference in its entirety.

The ALK2 inhibitors provided herein, their syntheses, and their biological activity against ALK2 can be found in PCT/CN2017/093385 (WO2018014829), which is incorporated by reference in its entirety.

Pharmaceutical Compositions

In an aspect, provided herein is a pharmaceutical composition comprising a JAK2 inhibitor, or pharmaceutically acceptable salt thereof, an ALK2 inhibitor, or a pharmaceutically acceptable salt thereof, and a pharmaceutically acceptable carrier.

In another aspect, provided herein is a pharmaceutical composition comprising an ALK2 inhibitor, a pharmaceutically acceptable carrier, and a JAK2 inhibitor having the Formula I:

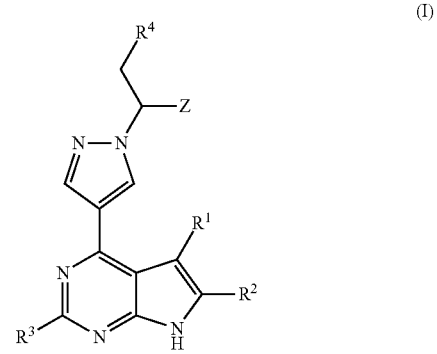

(I)

or a pharmaceutically acceptable salt thereof;

wherein $R^1$, $R^2$ and $R^3$ are independently selected from the group consisting of hydrogen, halo, and $C_{1-4}$ alkyl;

$R^4$ is selected from the group consisting of hydrogen, halo, cyano, nitro, hydroxy, $C_{1-4}$ alkyl, and $C_{1-4}$ alkoxy; and Z is 3-6 membered cycloalkyl.

In an embodiment of Formula I, $R^1$ is hydrogen. In another embodiment, $R^2$ is hydrogen. In yet another embodiment, $R^3$ is hydrogen. In still another embodiment, $R^4$ is cyano. In an embodiment, $R^1$, $R^2$ and $R^3$ are all hydrogen, and $R^4$ is cyano. In another embodiment, Z is cyclopentyl.

In an embodiment of the pharmaceutical composition, the ALK2 inhibitor is a compound of Formula II:

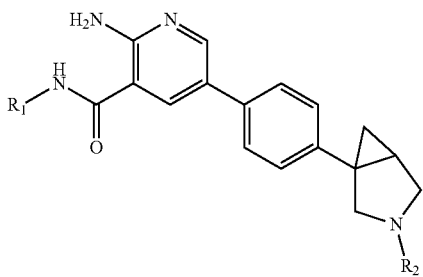

(II)

or a pharmaceutically acceptable salt thereof;
wherein $R_1$ is bridged 5-10 membered cycloalkyl optionally substituted one, two, or three times with hydroxyl or $C_1$-$C_3$ alkoxy;

$R^2$ is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with $R^3$; and $R^3$ is selected from the group consisting of hydroxy, halo, cyano, nitro, $SO_2$—$C_1$-$C_3$ alkyl, and $SO_3H$.

In an embodiment of Formula II, $R_1$ is bridged C-cycloalkyl substituted with hydroxyl. In another embodiment, $R_2$ is tetrahydropyran. In yet another embodiment, $R_1$ is bridged C-cycloalkyl substituted with hydroxyl and $R_2$ is tetrahydropyran.

In another aspect, provided herein is a pharmaceutical composition comprising a pharmaceutically acceptable carrier, (i) a JAK2 inhibitor having the Formula I:

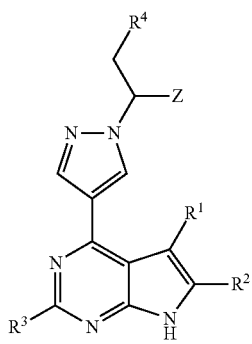

(I)

or a pharmaceutically acceptable salt thereof;
wherein $R^1$, $R^2$ and $R^3$ are independently selected from the group consisting of hydrogen, halo, and $C_{1-4}$ alkyl;

$R^4$ is selected from the group consisting of hydrogen, halo, cyano, nitro, hydroxy, $C_{1-4}$ alkyl, and $C_{1-4}$ alkoxy;

Z is 3-6 membered cycloalkyl; and (ii) an ALK2 inhibitor having the Formula IIa:

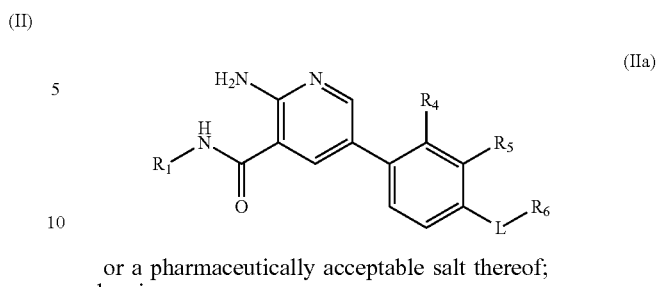

(IIa)

or a pharmaceutically acceptable salt thereof;
wherein

L is a bond, $(CH_2)_n$, —$CH(CH_3)$—, —O—$(CH_2)_n$—, —$C(O)$—, or —$C(O)$—NH—$(CH_2)_n$—;

n is 1, 2, or 3;

$R_1$ is selected from 3-7 membered cycloalkyl optionally substituted one, two, or three times with a substituent independently selected from hydroxyl, halogen, $C_1$-$C_3$ alkyl; bridged 5-10 membered cycloalkyl optionally substituted one, two, or three times with hydroxyl or $C_1$-$C_3$ alkoxy;

$R_4$ and $R_5$ are each independently selected from the group consisting of H, halogen, $C_1$-$C_3$ alkyl;

$R_6$ is 5-10 membered heterocycloalkyl optionally substituted one, two, or three times with $R_2$;

$R_2$ is independently, at each occurrence, selected from the group consisting of $C_1$-$C_3$ alkyl, $C_1$-$C_3$ alkoxy, $C_1$-$C_3$ alkoxy-$C_1$-$C_3$ alkyl, $C_1$-$C_3$ alkyl, $C_2$-$C_4$ alkynyl, $C_1$-$C_3$ alkyl, $(CH_2)_m$—$R_3$, wherein alkyl and alkoxy are optionally substituted one, two, or three times independently with halo or cyano;

m is 0, 1, 2 or 3;

$R_3$ is 4-6 membered heterocycloalkyl optionally substituted one, two, or three times with a substituent independently selected from the group consisting of oxo, $SO_2$—$C_1$-$C_3$ alkyl, $C_1$-$C_3$ alkyl, and 3-6 membered cycloalkyl, wherein alkyl and cycloalkyl are optionally substituted one, two, or three times with halo;

alternatively, two $R_3$, together with the atoms to which they are attached, form a 3-6 membered cycloalkyl.

In an embodiment of Formula IIa, L-$R_6$ is

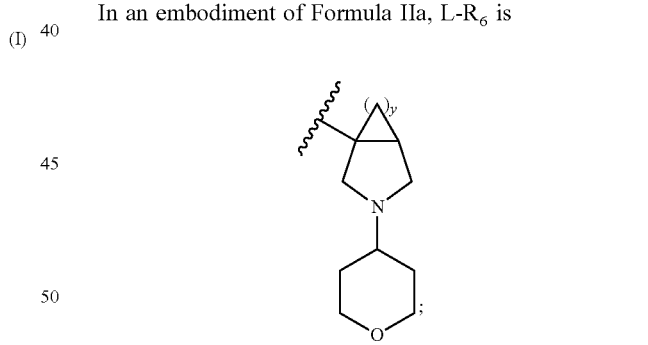

wherein y is 1, 2, or 3.

In an embodiment of the pharmaceutical compositions, the ALK2 inhibitor of Formula IIa is a compound of Formula IIb:

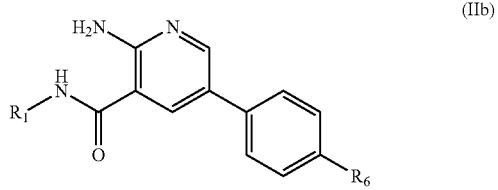

(IIb)

or a pharmaceutically acceptable salt thereof.

In an embodiment of Formula IIa and Formula IIb, $R_1$ is bridged C-cycloalkyl substituted with hydroxyl. In another embodiment, $R_2$ is tetrahydropyran. In yet another embodiment, $R_1$ is bridged C-cycloalkyl substituted with hydroxyl and $R_2$ is tetrahydropyran.

In yet another aspect, provided herein is a pharmaceutical composition comprising a pharmaceutically acceptable carrier, (i) a JAK2 inhibitor having the Formula I:

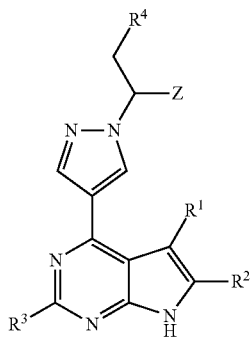

or a pharmaceutically acceptable salt thereof;
wherein
$R^1$, $R^2$ and $R^3$ are independently selected from the group consisting of hydrogen, halo, and $C_{1-4}$ alkyl;
$R^4$ is selected from the group consisting of hydrogen, halo, cyano, nitro, hydroxy, $C_{1-4}$ alkyl, and $C_{1-4}$ alkoxy;
Z is 3-6 membered cycloalkyl; and
(ii) an ALK2 inhibitor having the Formula II:

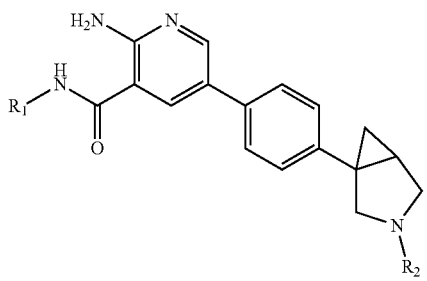

or a pharmaceutically acceptable salt thereof;
wherein
$R_1$ is bridged 5-10 membered cycloalkyl optionally substituted one, two, or three times with hydroxyl or $C_1$-$C_3$ alkoxy;
$R^2$ is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with $R^3$; and
$R^3$ is selected from the group consisting of hydroxy, halo, cyano, nitro, $SO_2$—$C_1$-$C_3$ alkyl, and $SO_3H$.

In an embodiment of Formula I, $R^1$ is hydrogen. In another embodiment, $R^2$ is hydrogen. In yet another embodiment, $R^3$ is hydrogen. In still another embodiment, $R^4$ is cyano. In an embodiment, $R^1$, $R^2$ and $R^3$ are all hydrogen, and $R^4$ is cyano. In another embodiment, Z is cyclopentyl.

In an embodiment of Formula II, $R_1$ is bridged Ca-cycloalkyl substituted with hydroxyl.

In another embodiment, $R_1$ is

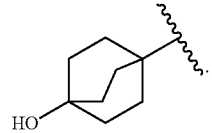

In yet another embodiment of Formula II, $R_2$ is tetrahydropyran. In another embodiment, $R_1$ is bridged Ca-cycloalkyl substituted with hydroxyl and $R_2$ is tetrahydropyran.

In another embodiment of the pharmaceutical composition, the JAK2 inhibitor of Formula I is 3-cyclopentyl-3-[4-(7H-pyrrolo[2,3-d]pyrimidin-4-yl)-1H-pyrazol-1-yl]propane-nitrile, or a pharmaceutically acceptable salt thereof.

In yet another embodiment of the pharmaceutical composition, the JAK2 inhibitor of Formula I is (3R)-3-cyclopentyl-3-[4-(7H-pyrrolo[2,3-d]pyrimidin-4-yl)-1H-pyrazol-1-yl]-propanenitrile, or a pharmaceutically acceptable salt thereof.

In another embodiment of the pharmaceutical composition, the JAK2 inhibitor of Formula I is (3R)-3-cyclopentyl-3-[4-(7H-pyrrolo[2,3-d]pyrimidin-4-yl)-1H-pyrazol-1-yl]-propanenitrile phosphoric acid salt.

In still another embodiment of the pharmaceutical composition, the ALK2 inhibitor of Formula II is 2-amino-N-(4-hydroxy-bicyclo[2.2.2]octan-1-yl)-5-(4-(3-(tetrahydro-2H-pyran-4-yl)-3-aza-bicyclo[3.1.0]hexan-1-yl)phenyl)nicotinamide, or a pharmaceutically acceptable salt thereof.

In an embodiment of the pharmaceutical composition, the ALK2 inhibitor of Formula II is 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)nicotinamide (Compound A), or a pharmaceutically acceptable salt thereof.

In another embodiment of the pharmaceutical composition, the ALK2 inhibitor of Formula II is 2-amino-N-(4-hydroxybicyclo-[2.2.2]octan-1-yl)-5-(4-((1S,5R)-3-(tetrahydro-2H-pyran-4-yl)-3-azabicyclo-[3.1.0]hexan-1-yl)phenyl)nicotinamide, or a pharmaceutically acceptable salt thereof.

In yet another embodiment of the pharmaceutical composition, the JAK2 inhibitor of Formula I is 3-cyclopentyl-3-[4-(7H-pyrrolo[2,3-d]pyrimidin-4-yl)-1H-pyrazol-1-yl]propane-nitrile, or a pharmaceutically acceptable salt thereof, and the ALK2 inhibitor of Formula II is 2-amino-N-(4-hydroxybicyclo-[2.2.2]octan-1-yl)-5-(4-(3-(tetrahydro-2H-pyran-4-yl)-3-azabicyclo-[3.1.0]hexan-1-yl)phenyl)nicotinamide, or a pharmaceutically acceptable salt thereof.

In still another embodiment of the pharmaceutical composition, the JAK2 inhibitor of Formula I is 3-cyclopentyl-3-[4-(7H-pyrrolo[2,3-d]pyrimidin-4-yl)-1H-pyrazol-1-yl]propane-nitrile phosphoric acid salt, and the ALK2 inhibitor of Formula II is 2-amino-N-(4-hydroxybicyclo-[2.2.2]octan-1-yl)-5-(4-(3-(tetrahydro-2H-pyran-4-yl)-3-azabicyclo-[3.1.0]hexan-1-yl)phenyl)-nicotinamide, or a pharmaceutically acceptable salt thereof.

In an embodiment of the pharmaceutical composition, the JAK2 inhibitor of Formula I is (3R)-3-cyclopentyl-3-[4-(7H-pyrrolo[2,3-d]pyrimidin-4-yl)-1H-pyrazol-1-yl]propa-nenitrile, or a pharmaceutically acceptable salt thereof, and the ALK2 inhibitor of Formula II is 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)nicotinamide (Compound A), or a pharmaceutically acceptable salt thereof.

In another embodiment of the pharmaceutical composition, the JAK2 inhibitor of Formula I is (3R)-3-cyclopentyl-3-[4-(7H-pyrrolo[2,3-d]pyrimidin-4-yl)-1H-pyrazol-1-yl] propanenitrile phosphoric acid salt, and the ALK2 inhibitor of Formula II is 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)nicotinamide (Compound A), or a pharmaceutically acceptable salt thereof.

In one embodiment, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In another embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In yet another embodiment, the compounds described herein include a $^{2}H$ (i.e., deuterium) isotope.

In still another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The specific compounds described herein, and other compounds encompassed by one or more of the formulas described herein having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as described herein are modified by the use of appropriate reagents and conditions, for the introduction of the various moieties found in the Formulas as provided herein.

In some embodiments, the JAK2 inhibitor is ruxolitinib (a JAK1/2 inhibitor). Ruxolitinib ((R)-3-(4-(7H-pyrrolo[2,3-d]pyrimidin-4-yl)-1H-pyrazol-1-yl)-3-cyclopentylpropanenitrile) (sometimes referred to as INCB018424), and its pharmaceutically acceptable salts have been previously been described in U.S. Pat. No. 7,598,257, which is incorporated herein by reference in its entirety. Ruxolitinib phosphate is described in U.S. Pat. No. 8,722,693, which is incorporated herein by reference in its entirety. The present disclosure describes, inter alia, combination methods using ruxolitinib, or a pharmaceutically acceptable salt thereof. In some embodiments, the JAK2 inhibitor is ruxolitinib, wherein one or more hydrogen atoms are replaced by deuterium atoms, or a pharmaceutically acceptable salt thereof. In some embodiments, the JAK2 inhibitor is any of the compounds in U.S. Pat. No. 9,249,149 (which is incorporated herein by reference in its entirety), or a pharmaceutically acceptable salt thereof. In some embodiments, the JAK2 inhibitor is CTP-543, or a pharmaceutically acceptable salt thereof. In some embodiments, the compound is a compound of Formula III:

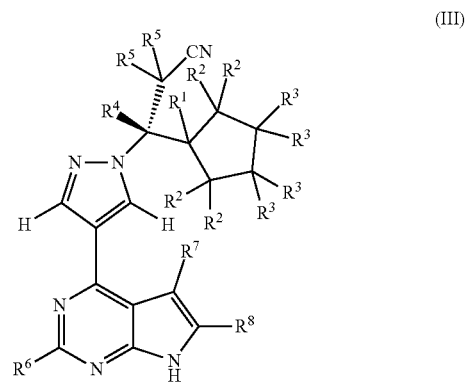

(III)

or a pharmaceutically acceptable salt thereof, wherein:
$R^1$ is selected from H and D;
each $R^2$ is independently selected from H and D, provided that each $R^2$ attached to a common carbon is the same;
each $R^3$ is independently selected from H and D, provided that each $R^3$ attached to a common carbon is the same;
$R^4$ is selected from H and D;
each $R^5$ is the same and is selected from H and D; and
$R^6$, $R^7$, and $R^8$ are each independently selected from H and D; provided that when $R^1$ is H, each $R^2$ and each $R^3$ are H, $R^4$ is H, and each of $R^7$, and R is H, then each $R^5$ is D.

In some embodiments, the JAK2 inhibitor is a compound of Formula III selected from the following compounds 100-130 in the table below (wherein $R^6$, $R^7$, and $R^8$ are each H), or a pharmaceutically acceptable salt thereof. In some embodiments, the JAK2 inhibitor is a compound of Formula III selected from the following compounds 200-231 in the table below (wherein $R^6$, $R^7$, and $R^8$ are each D), or a pharmaceutically acceptable salt thereof.

| Compound | $R^1$ | Each $R^2$ | Each $R^3$ | $R^4$ | Each $R^5$ |
|---|---|---|---|---|---|
| 100 | H | H | H | D | H |
| 101 | H | H | H | H | D |
| 102 | H | H | H | D | D |
| 103 | H | H | D | H | H |
| 104 | H | H | D | D | H |
| 105 | H | H | D | H | D |
| 106 | H | H | D | D | D |
| 107 | H | D | H | H | H |
| 108 | H | D | H | D | H |
| 109 | H | D | H | H | D |
| 110 | H | D | H | D | D |
| 111 | H | D | D | H | H |
| 112 | H | D | D | D | H |
| 113 | H | D | D | H | D |
| 114 | H | D | D | D | D |
| 115 | D | H | H | H | H |
| 116 | D | H | H | D | H |
| 117 | D | H | H | H | D |
| 118 | D | H | H | D | D |

-continued

| Compound | R¹ | Each R² | Each R³ | R⁴ | Each R⁵ |
|---|---|---|---|---|---|
| 119 | D | H | D | H | H |
| 120 | D | H | D | D | H |
| 121 | D | H | D | H | D |
| 122 | D | H | D | D | D |
| 123 | D | D | H | H | H |
| 124 | D | D | H | D | H |
| 125 | D | D | H | H | D |
| 126 | D | D | H | D | D |
| 127 | D | D | D | H | H |
| 128 | D | D | D | D | H |
| 129 | D | D | D | H | D |
| 130 | D | D | D | D | D |
| 200 | H | H | H | D | H |
| 201 | H | H | H | H | D |
| 202 | H | H | H | D | D |
| 203 | H | H | D | H | H |
| 204 | H | H | D | D | H |
| 205 | H | H | D | H | D |
| 206 | H | H | D | D | D |
| 207 | H | D | H | H | H |
| 208 | H | D | H | D | H |
| 209 | H | D | H | H | D |
| 210 | H | D | H | D | D |
| 211 | H | D | D | H | H |
| 212 | H | D | D | D | H |
| 213 | H | D | D | H | D |
| 214 | H | D | D | D | D |
| 215 | D | H | H | H | H |
| 216 | D | H | H | D | H |
| 217 | D | H | H | H | D |
| 218 | D | H | H | D | D |
| 219 | D | H | D | H | H |
| 220 | D | H | D | D | H |
| 221 | D | H | D | H | D |
| 222 | D | H | D | D | D |
| 223 | D | D | H | H | H |
| 224 | D | D | H | D | H |
| 225 | D | D | H | H | D |
| 226 | D | D | H | D | D |
| 227 | D | D | D | H | H |
| 228 | D | D | D | D | H |
| 229 | D | D | D | H | D |
| 230 | D | D | D | D | D |
| 231 | H | H | H | H | H |

In some embodiments, the JAK2 inhibitor is baricitinib.

In some embodiments, the JAK2 inhibitor is fedratinib.

In some embodiments, the JAK2 inhibitor is momelotinib.

In some embodiments, the JAK2 inhibitor is BMS-911543.

In some embodiments, the JAK2 inhibitor is pacritinib.

In some embodiments, the JAK2 inhibitor is NS-018.

In some embodiments, the JAK2 inhibitor is NVP-BBT594.

In some embodiments, the JAK2 inhibitor is NVP-CHZ868.

Compounds described herein are synthesized using any suitable procedures starting from compounds that are available from commercial sources, or are prepared using procedures described herein.

Methods of Treatment

Also provided herein is a combination therapy comprising administering to a subject in need thereof an ALK2 inhibitor, or pharmaceutically acceptable salt thereof, and a JAK2 inhibitor, or pharmaceutically acceptable salt thereof.

In an embodiment of the combination therapy, the JAK2 inhibitor is a compound of Formula I:

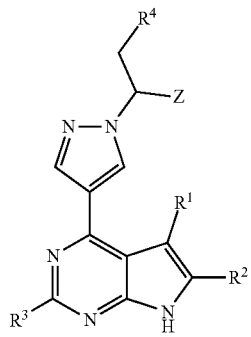

(I)

or a pharmaceutically acceptable salt thereof;
wherein
$R^1$, $R^2$ and $R^3$ are independently selected from the group consisting of hydrogen, halo, and $C_{1-4}$ alkyl;
$R^4$ is selected from the group consisting of hydrogen, halo, cyano, nitro, hydroxy, $C_{1-4}$ alkyl, and $C_{1-4}$ alkoxy; and
Z is 3-6 membered cycloalkyl.

In an embodiment of Formula I, $R^1$ is hydrogen. In another embodiment, $R^2$ is hydrogen. In yet another embodiment, $R^3$ is hydrogen. In still another embodiment, $R^4$ is cyano. In an embodiment, $R^1$, $R^2$ and $R^3$ are all hydrogen, and $R^4$ is cyano. In another embodiment, Z is cyclopentyl.

In another embodiment of the combination therapy, the ALK2 inhibitor is a compound of Formula II:

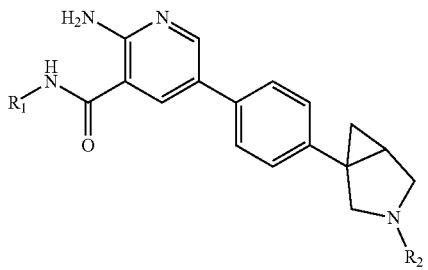

(II)

or a pharmaceutically acceptable salt thereof;
wherein
$R_1$ is bridged 5-10 membered cycloalkyl optionally substituted one, two, or three times with hydroxyl or $C_1$-$C_3$ alkoxy;
$R_2$ is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with $R^3$; and
$R^3$ is selected from the group consisting of hydroxy, halo, cyano, nitro, $SO_2$—$C_1$-$C_3$ alkyl, and $SO_3H$.

In an embodiment of Formula II, $R_1$ is bridged $C_8$-cycloalkyl substituted with hydroxyl. In another embodiment, $R_1$ is

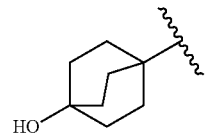

In yet another embodiment of Formula II, $R_2$ is tetrahydropyran. In another embodiment, $R_1$ is bridged Ca-cycloalkyl substituted with hydroxyl and $R_2$ is tetrahydropyran.

In another embodiment of the combination therapy, the JAK2 inhibitor of Formula I is 3-cyclopentyl-3-[4-(7H-pyrrolo[2,3-d]pyrimidin-4-yl)-1H-pyrazol-1-yl]propanenitrile, or a pharmaceutically acceptable salt thereof.

In yet another embodiment of the combination therapy, the JAK2 inhibitor of Formula I is (3R)-3-cyclopentyl-3-[4-(7H-pyrrolo[2,3-d]pyrimidin-4-yl)-1H-pyrazol-1-yl]-propanenitrile, or a pharmaceutically acceptable salt thereof.

In another embodiment of the combination therapy, the JAK2 inhibitor of Formula I is (3R)-3-cyclopentyl-3-[4-(7H-pyrrolo[2,3-d]pyrimidin-4-yl)-1H-pyrazol-1-yl]-propanenitrile phosphoric acid salt.

In still another embodiment of the combination therapy, the ALK2 inhibitor of Formula II is 2-amino-N-(4-hydroxybicyclo[2.2.2]octan-1-yl)-5-(4-(3-(tetrahydro-2H-pyran-4-yl)-3-aza-bicyclo[3.1.0]hexan-1-yl)phenyl)nicotinamide, or a pharmaceutically acceptable salt thereof.

In an embodiment of the combination therapy, the ALK2 inhibitor of Formula II is 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)nicotinamide (Compound A), or a pharmaceutically acceptable salt thereof.

In another embodiment of the combination therapy, the ALK2 inhibitor of Formula II is 2-amino-N-(4-hydroxybicyclo-[2.2.2]octan-1-yl)-5-(4-((1S,5R)-3-(tetrahydro-2H-pyran-4-yl)-3-azabicyclo-[3.1.0]hexan-1-yl)phenyl)nicotinamide, or a pharmaceutically acceptable salt thereof.

In yet another embodiment of the combination therapy, the JAK2 inhibitor of Formula I is 3-cyclopentyl-3-[4-(7H-pyrrolo[2,3-d]pyrimidin-4-yl)-1H-pyrazol-1-yl]propanenitrile, or a pharmaceutically acceptable salt thereof, and the ALK2 inhibitor of Formula II is 2-amino-N-(4-hydroxybicyclo-[2.2.2]octan-1-yl)-5-(4-(3-(tetrahydro-2H-pyran-4-yl)-3-azabicyclo-[3.1.0]hexan-1-yl)phenyl)nicotinamide, or a pharmaceutically acceptable salt thereof.

In still another embodiment of the combination therapy, the JAK2 inhibitor of Formula I is 3-cyclopentyl-3-[4-(7H-pyrrolo[2,3-d]pyrimidin-4-yl)-1H-pyrazol-1-yl]propanenitrile phosphoric acid salt, and the ALK2 inhibitor of Formula II is 2-amino-N-(4-hydroxybicyclo-[2.2.2]octan-1-yl)-5-(4-(3-(tetrahydro-2H-pyran-4-yl)-3-azabicyclo-[3.1.0]hexan-1-yl)-nicotinamide, or a pharmaceutically acceptable salt thereof.

In an embodiment of the combination therapy, the JAK2 inhibitor of Formula I is (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, and the ALK2 inhibitor of Formula II is 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)nicotinamide (Compound A), or a pharmaceutically acceptable salt thereof.

In another embodiment of the combination therapy, the JAK2 inhibitor of Formula I is (3R)-3-cyclopentyl-3-[4-(7H-pyrrolo[2,3-d]pyrimidin-4-yl)-1H-pyrazol-1-yl]propanenitrile phosphoric acid salt, and the ALK2 inhibitor of Formula II is 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)nicotinamide (Compound A), or a pharmaceutically acceptable salt thereof.

The combination therapy provided herein can be used in a method of treating a disease or condition in a subject, said method comprising administering to the subject in need thereof a combination or composition comprising compounds provided herein, or pharmaceutically acceptable salts thereof.

In an aspect, provided herein is a method of treating cancer in a subject in need thereof, comprising administering to the subject an ALK2 inhibitor, or pharmaceutically acceptable salt thereof, and a JAK2 inhibitor, or pharmaceutically acceptable salt thereof.

In an aspect, provided herein is a method of treating anemia in a subject in need thereof, comprising administering to the subject an ALK2 inhibitor, or pharmaceutically acceptable salt thereof, and a JAK2 inhibitor, or pharmaceutically acceptable salt thereof.

In another aspect, provided herein is a method of treating cancer in a subject in need thereof, comprising administering to the subject an ALK2 inhibitor, or pharmaceutically acceptable salt thereof, and a JAK2 inhibitor having the Formula I:

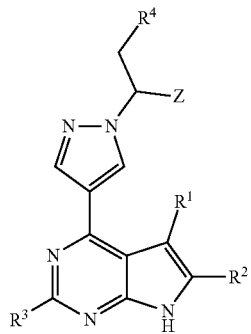

(I)

or a pharmaceutically acceptable salt thereof;
wherein
$R^1$, $R^2$ and $R^3$ are independently selected from the group consisting of hydrogen, halo, and $C_{1-4}$ alkyl;
$R^4$ is selected from the group consisting of hydrogen, halo, cyano, nitro, hydroxy, $C_{1-4}$ alkyl, and $C_{1-4}$ alkoxy; and
Z is 3-6 membered cycloalkyl.

In an embodiment of the methods, the ALK2 inhibitor is a compound of Formula II:

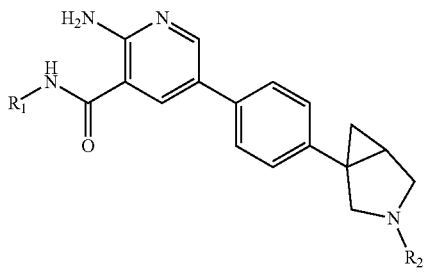

(II)

or a pharmaceutically acceptable salt thereof;
wherein
$R_1$ is bridged 5-10 membered cycloalkyl optionally substituted one, two, or three times with hydroxyl or $C_1$-$C_3$ alkoxy;
$R^2$ is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with $R^3$; and $R^3$ is selected from the group consisting of hydroxy, halo, cyano, nitro, $SO_2$—$C_1$-$C_3$ alkyl, and $SO_3H$.

In yet another aspect, provided herein is a method of treating cancer in a subject in need thereof, comprising administering to the subject:

(i) a JAK2 inhibitor having the Formula I:

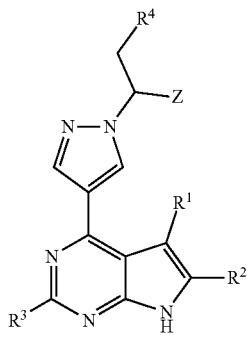

(I)

or a pharmaceutically acceptable salt thereof;
wherein
$R^1$, $R^2$ and $R^3$ are independently selected from the group consisting of hydrogen, halo, and $C_{1-4}$ alkyl;
$R^4$ is selected from the group consisting of hydrogen, halo, cyano, nitro, hydroxy, $C_{1-4}$ alkyl, and $C_{1-4}$ alkoxy;
Z is 3-6 membered cycloalkyl; and
(ii) an ALK2 inhibitor having the Formula IIa:

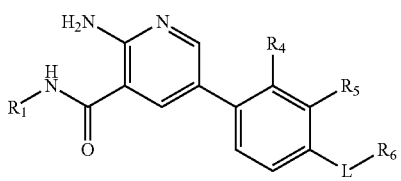

(IIa)

or a pharmaceutically acceptable salt thereof;
wherein
L is a bond, $(CH_2)_n$, —$CH(CH_3)$—, —O—$(CH_2)_n$—, —C(O)—, or —C(O)—NH—$(CH_2)_n$—;
n is 1, 2, or 3;
$R_1$ is selected from 3-7 membered cycloalkyl optionally substituted one, two, or three times with a substituent independently selected from hydroxyl, halogen, $C_1$-$C_3$ alkyl; bridged 5-10 membered cycloalkyl optionally substituted one, two, or three times with hydroxyl or $C_1$-$C_3$ alkoxy;
$R_4$ and $R_5$ are each independently selected from the group consisting of H, halogen, $C_1$-$C_3$ alkyl;
$R_6$ is 5-10 membered heterocycloalkyl optionally substituted one, two, or three times with $R_2$;
$R_2$ is independently, at each occurrence, selected from the group consisting of $C_1$-$C_3$ alkyl, $C_1$-$C_3$ alkoxy, $C_1$-$C_3$ alkoxy-$C_1$-$C_3$ alkyl, $C_1$-$C_3$ alkyl, $C_2$-$C_4$ alkynyl, $C_1$-$C_3$ alkyl, $(CH_2)_m$—$R_3$, wherein alkyl and alkoxy are optionally substituted one, two, or three times independently with halo or cyano;
m is 0, 1, 2 or 3;
$R_3$ is 4-6 membered heterocycloalkyl optionally substituted one, two, or three times with a substituent independently selected from the group consisting of oxo, $SO_2$—$C_1$-$C_3$ alkyl, $C_1$-$C_3$ alkyl, and 3-6 membered cycloalkyl, wherein alkyl and cycloalkyl are optionally substituted one, two, or three times with halo;
alternatively, two $R_3$, together with the atoms to which they are attached, form a 3-6 membered cycloalkyl.

In an embodiment of Formula IIa, L-$R_6$ is

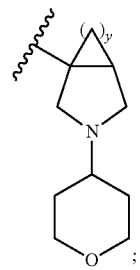

wherein y is 1, 2, or 3.

In an embodiment of the methods, the ALK2 inhibitor of Formula IIa is a compound of Formula IIb:

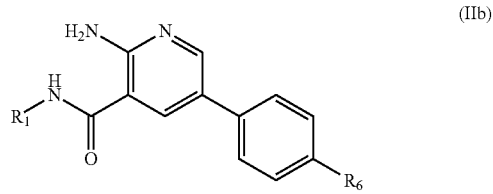

(IIb)

or a pharmaceutically acceptable salt thereof.

In an embodiment of Formula IIa and Formula IIb, $R_1$ is bridged Ca-cycloalkyl substituted with hydroxyl. In another embodiment, $R_2$ is tetrahydropyran. In yet another embodiment, $R_1$ is bridged Ca-cycloalkyl substituted with hydroxyl and $R_2$ is tetrahydropyran.

In yet another aspect, provided herein is a method of treating cancer in a subject in need thereof, comprising administering to the subject (i) a JAK2 inhibitor having the Formula I:

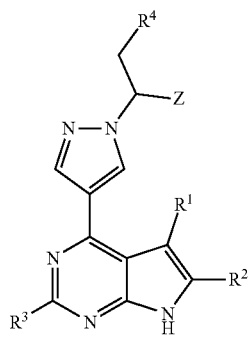

(I)

or a pharmaceutically acceptable salt thereof;
wherein
$R^1$, $R^2$ and $R^3$ are independently selected from the group consisting of hydrogen, halo, and $C_{1-4}$ alkyl;
$R^4$ is selected from the group consisting of hydrogen, halo, cyano, nitro, hydroxy, $C_{1-4}$ alkyl, and $C_{1-4}$ alkoxy;
Z is 3-6 membered cycloalkyl; and (ii) an ALK2 inhibitor having the Formula II:

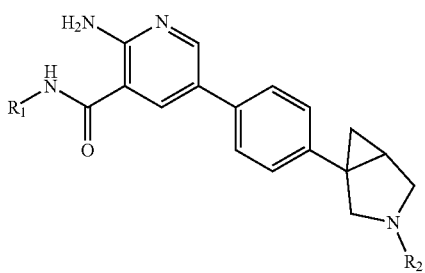

or a pharmaceutically acceptable salt thereof;
wherein
$R_1$ is bridged 5-10 membered cycloalkyl optionally substituted one, two, or three times with hydroxyl or $C_1$-$C_3$ alkoxy;
$R^2$ is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with $R^3$; and
$R^3$ is selected from the group consisting of hydroxy, halo, cyano, nitro, $SO_2$—$C_1$-$C_3$ alkyl, and $SO_3H$.

In an embodiment of Formula I, $R^1$ is hydrogen. In another embodiment, $R^2$ is hydrogen. In yet another embodiment, $R^3$ is hydrogen. In still another embodiment, $R^4$ is cyano. In an embodiment, $R^1$, $R^2$ and $R^3$ are all hydrogen, and $R^4$ is cyano. In another embodiment, Z is cyclopentyl.

In another embodiment of the methods, the JAK2 inhibitor of Formula I is 3-cyclopentyl-3-[4-(7H-pyrrolo[2,3-d]pyrimidin-4-yl)-1H-pyrazol-1-yl]propanenitrile, or a pharmaceutically acceptable salt thereof.

In yet another embodiment of the methods, the JAK2 inhibitor of Formula I is (3R)-3-cyclopentyl-3-[4-(7H-pyrrolo[2,3-d]pyrimidin-4-yl)-1H-pyrazol-1-yl]propanenitrile, or a pharmaceutically acceptable salt thereof.

In another embodiment of the methods, the JAK2 inhibitor of Formula I is (3R)-3-cyclopentyl-3-[4-(7H-pyrrolo[2,3-d]pyrimidin-4-yl)-1H-pyrazol-1-yl]-propanenitrile phosphoric acid salt.

In still another embodiment of the methods, the ALK2 inhibitor of Formula II is 2-amino-N-(4-hydroxy-bicyclo[2.2.2]octan-1-yl)-5-(4-(3-(tetrahydro-2H-pyran-4-yl)-3-aza-bicyclo[3.1.0]hexan-1-yl)phenyl)nicotinamide, or a pharmaceutically acceptable salt thereof.

In an embodiment of the methods, the ALK2 inhibitor of Formula II is 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)nicotinamide (Compound A), or a pharmaceutically acceptable salt thereof.

In another embodiment of the methods, the ALK2 inhibitor of Formula II is 2-amino-N-(4-hydroxybicyclo-[2.2.2]octan-1-yl)-5-(4-((1S,5R)-3-(tetrahydro-2H-pyran-4-yl)-3-azabicyclo-[3.1.0]hexan-1-yl)phenyl)nicotinamide, or a pharmaceutically acceptable salt thereof.

In yet another embodiment of the methods, the JAK2 inhibitor of Formula I is 3-cyclopentyl-3-[4-(7H-pyrrolo[2,3-d]pyrimidin-4-yl)-1H-pyrazol-1-yl]propane-nitrile, or a pharmaceutically acceptable salt thereof, and the ALK2 inhibitor of Formula II is 2-amino-N-(4-hydroxybicyclo-[2.2.2]octan-1-yl)-5-(4-(3-(tetrahydro-2H-pyran-4-yl)-3-azabicyclo[3.1.0]-hexan-1-yl)phenyl)nicotinamide, or a pharmaceutically acceptable salt thereof.

In still another embodiment of the methods, the JAK2 inhibitor of Formula I is 3-cyclo-pentyl-3-[4-(7H-pyrrolo[2,3-d]pyrimidin-4-yl)-1H-pyrazol-1-yl]propane-nitrile phosphoric acid salt, and the ALK2 inhibitor of Formula II is 2-amino-N-(4-hydroxybicyclo-[2.2.2]octan-1-yl)-5-(4-(3-(tetrahydro-2H-pyran-4-yl)-3-azabicyclo-[3.1.0]hexan-1-yl)phenyl)-nicotinamide, or a pharmaceutically acceptable salt thereof.

In an embodiment of the methods, the JAK2 inhibitor of Formula I is (3R)-3-cyclo-pentyl-3-[4-(7H-pyrrolo[2,3-d]pyrimidin-4-yl)-1H-pyrazol-1-yl]propanenitrile, or a pharmaceutically acceptable salt thereof, and the ALK2 inhibitor of Formula II is 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)nicotinamide (Compound A), or a pharmaceutically acceptable salt thereof.

In another embodiment of the methods, the JAK2 inhibitor of Formula I is (3R)-3-cyclo-pentyl-3-[4-(7H-pyrrolo[2,3-d]pyrimidin-4-yl)-1H-pyrazol-1-yl]propanenitrile phosphoric acid salt, and the ALK2 inhibitor of Formula II is 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)-nicotinamide (Compound A), or a pharmaceutically acceptable salt thereof.

In an embodiment of the methods, the ALK2 inhibitor and JAK2 inhibitor are administered separately.

In an aspect, provided herein is a method of treating cancer in a subject in need thereof, comprising administering to the subject an ALK2 inhibitor, or pharmaceutically acceptable salt thereof.

In an embodiment of the method of treating cancer, the ALK2 inhibitor is a compound of Formula IIa:

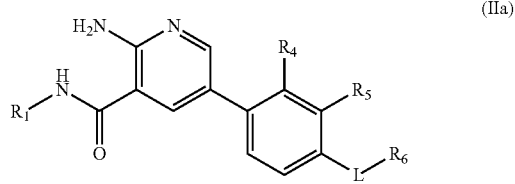

or a pharmaceutically acceptable salt thereof;
wherein
L is a bond, $(CH_2)_n$, —$CH(CH_3)$—, —O—$(CH_2)_n$—, —C(O)—, or —C(O)—NH—$(CH_2)_n$—;
n is 1, 2, or 3;
$R_1$ is selected from 3-7 membered cycloalkyl optionally substituted one, two, or three times with a substituent independently selected from hydroxyl, halogen, $C_1$-$C_3$ alkyl; bridged 5-10 membered cycloalkyl optionally substituted one, two, or three times with hydroxyl or $C_1$-$C_3$ alkoxy;
$R_4$ and $R_5$ are each independently selected from the group consisting of H, halogen, $C_1$-$C_3$ alkyl;
$R_6$ is 5-10 membered heterocycloalkyl optionally substituted one, two, or three times with $R_2$;
$R_2$ is independently, at each occurrence, selected from the group consisting of $C_1$-$C_3$ alkyl, $C_1$-$C_3$ alkoxy, $C_1$-$C_3$ alkoxy-$C_1$-$C_3$ alkyl, $C_1$-$C_3$ alkyl, $C_2$-$C_4$ alkynyl, $C_1$-$C_3$ alkyl, $(CH_2)_m$—$R_3$, wherein alkyl and alkoxy are optionally substituted one, two, or three times independently with halo or cyano;
m is 0, 1, 2 or 3;
$R_3$ is 4-6 membered heterocycloalkyl optionally substituted one, two, or three times with a substituent independently selected from the group consisting of oxo, $SO_2$—$C_1$-

$C_3$ alkyl, $C_1$-$C_3$ alkyl, and 3-6 membered cycloalkyl, wherein alkyl and cycloalkyl are optionally substituted one, two, or three times with halo;

alternatively, two $R_3$, together with the atoms to which they are attached, form a 3-6 membered cycloalkyl.

In an embodiment of the cancer treatment Formula IIa, L-$R_6$ is

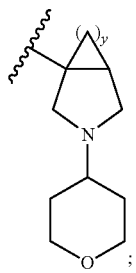

wherein y is 1, 2, or 3.

In an embodiment of the cancer treatment, the ALK2 inhibitor of Formula IIa is a compound of Formula IIb:

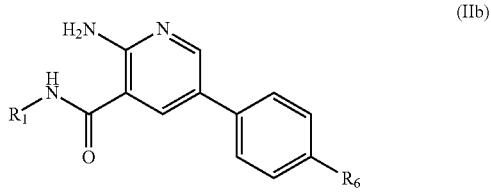

(IIb)

or a pharmaceutically acceptable salt thereof.

In an embodiment of Formula IIa and Formula IIb, $R_1$ is bridged C-cycloalkyl substituted with hydroxyl. In another embodiment, $R_2$ is tetrahydropyran. In yet another embodiment, $R_1$ is bridged C-cycloalkyl substituted with hydroxyl and $R_2$ is tetrahydropyran.

In another embodiment of the method of treating cancer, the ALK2 inhibitor of Formula IIa is a compound of Formula II:

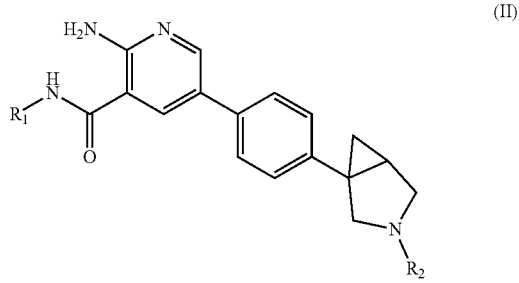

(II)

or a pharmaceutically acceptable salt thereof;
wherein
$R_1$ is bridged 5-10 membered cycloalkyl optionally substituted one, two, or three times with hydroxyl or $C_1$-$C_3$ alkoxy;

$R^2$ is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with $R^3$; and $R^3$ is selected from the group consisting of hydroxy, halo, cyano, nitro, $SO_2$—$C_1$-$C_3$ alkyl, and $SO_3H$.

In still another embodiment of the method of treating cancer, the ALK2 inhibitor of Formula II is 2-amino-N-(4-hydroxy-bicyclo[2.2.2]octan-1-yl)-5-(4-(3-(tetrahydro-2H-pyran-4-yl)-3-aza-bicyclo[3.1.0]hexan-1-yl)phenyl)nicotinamide, or a pharmaceutically acceptable salt thereof.

In an embodiment of the method of treating cancer, the ALK2 inhibitor of Formula II is 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)nicotinamide (Compound A), or a pharmaceutically acceptable salt thereof.

In another embodiment of the method of treating cancer, the ALK2 inhibitor of Formula II is 2-amino-N-(4-hydroxybicyclo-[2.2.2]octan-1-yl)-5-(4-((1S,5R)-3-(tetrahydro-2H-pyran-4-yl)-3-azabicyclo-[3.1.0]hexan-1-yl)phenyl)nicotinamide, or a pharmaceutically acceptable salt thereof.

In yet another embodiment of the method of treating cancer, the ALK2 inhibitor of Formula II is 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)-nicotinamide fumarate dihydrate.

In another embodiment of the method of treating cancer, the ALK2 inhibitor is administered as a monotherapy. In yet another embodiment of the method of treating cancer, the ALK2 inhibitor is administered in the absence of any other active pharmaceutical ingredient. In still another embodiment of the method of treating cancer, the ALK2 inhibitor is administered in the absence of a Janus Kinase inhibitor.

In another embodiment of the methods, the cancer is a myeloproliferative neoplasm.

In another embodiment of the methods, the cancer is a myelodysplastic syndrome. Myelodysplastic syndromes (MDS) can include hematopoietic stem cell disorders characterized by one or more of the following: ineffective blood cell production, progressive cytopenias, risk of progression to acute leukemia or cellular marrow with impaired morphology and maturation (dysmyelopoiesis). Myelodysplastic syndromes can also include refractory anemia, refractory anemia with ringed sideroblasts, refractory anemia with excess blasts, refractory anemia with excess blasts in transformation and chronic myelomonocytic leukemia.

In yet another embodiment of the methods, the cancer is selected from the group consisting of chronic myeloid leukemia (CML), polycythemia vera (PV), essential thrombocythemia (ET), myelofibrosis (MF), chronic neutrophilic leukemia, chronic eosinophilic leukemia, chronic myelomonocytic leukemia, juvenile myelomonocytic leukemia, hypereosinophilic syndrome, systemic mastocytosis, atypical chronic myelogenous leukemia, acute lymphoblastic leukemia (ALL), and acute myeloid leukemia (AML). In still another embodiment, the cancer is myelofibrosis (MF).

In an embodiment of the methods, the cancer is selected from the group consisting of primary myelofibrosis, post-polycythemia vera myelofibrosis, or post-essential thrombocythemia myelofibrosis.

In an aspect, provided herein is a method of treating anemia in a subject in need thereof, comprising administering to the subject a JAK2 inhibitor of Formula I and an ALK2 inhibitor of Formula II.

In another embodiment of the methods, the anemia is cancer-induced anemia.

In another embodiment of the methods, the anemia is due to myeloproliferative or myelodysplastic hematological malignancies.

In another embodiment of the methods, the anemia is a myelofibrosis-induced anemia.

In an embodiment of the methods of treating anemia, the JAK2 inhibitor of Formula I is 3-cyclopentyl-3-[4-(7H-pyrrolo[2,3-d]pyrimidin-4-yl)-1H-pyrazol-1-yl]propanenitrile, or a pharmaceutically acceptable salt thereof; and the ALK2 inhibitor of Formula II is 2-amino-N-(4-hydroxybicyclo[2.2.2]octan-1-yl)-5-(4-(3-(tetrahydro-2H-pyran-4-yl)-3-azabicyclo[3.1.0]-hexan-1-yl)phenyl)nicotinamide, or a pharmaceutically acceptable salt or hydrate thereof.

In another embodiment of the methods, the subject is human.

In yet another embodiment of the methods, the treatment comprises administering the ALK2 inhibitor and the JAK2 inhibitor at substantially the same time.

In still another embodiment of the methods, the treatment comprises administering the ALK2 inhibitor and the JAK2 inhibitor at different times.

In an embodiment of the methods, the ALK2 inhibitor is administered to the subject, followed by administration of the JAK2 inhibitor. In another embodiment, the JAK2 inhibitor is administered to the subject, followed by administration of the ALK2 inhibitor.

In another embodiment of the methods, the ALK2 inhibitor and/or JAK2 inhibitor are administered at dosages that would not be effective when one or both of the ALK2 inhibitor and the JAK2 inhibitor are administered alone, but which amounts are effective in combination.

In yet another aspect, provided herein is a method of treating a cancer comprising administering to a subject in need thereof 2-amino-N-(4-hydroxy-bicyclo-[2.2.2]octan-1-yl)-5-(4-((1R,5S)-3-(tetrahydro-2H-pyran-4-yl)-3-azabicyclo[3.1.0]-hexan-1-yl)phenyl)nicotinamide (Compound A), or a pharmaceutically acceptable salt thereof, and (3R)-3-cyclopentyl-3-[4-(7H-pyrrolo[2,3-d]pyrimidin-4-yl)-1H-pyrazol-1-yl]propanenitrile, or pharmaceutically acceptable salts thereof.

In still another aspect, provided herein is a method of treating a cancer comprising administering to a subject in need thereof 2-amino-N-(4-hydroxy-bicyclo-[2.2.2]octan-1-yl)-5-(4-((1R,5S)-3-(tetrahydro-2H-pyran-4-yl)-3-azabicyclo[3.1.0]-hexan-1-yl)phenyl)nicotinamide (Compound A), or a pharmaceutically acceptable salt thereof, and (3R)-3-cyclopentyl-3-[4-(7H-pyrrolo[2,3-d]pyrimidin-4-yl)-1H-pyrazol-1-yl]propanenitrile phosphoric acid salt.

In an aspect, provided herein is a method of treating myelofibrosis (MF) comprising administering to a subject in need thereof 2-amino-N-(4-hydroxy-bicyclo-[2.2.2]octan-1-yl)-5-(4-((1R,5S)-3-(tetrahydro-2H-pyran-4-yl)-3-azabicyclo[3.1.0]-hexan-1-yl)phenyl)nicotinamide (Compound A), or a pharmaceutically acceptable salt thereof, and (3R)-3-cyclopentyl-3-[4-(7H-pyrrolo[2,3-d]pyrimidin-4-yl)-1H-pyrazol-1-yl]propanenitrile, or pharmaceutically acceptable salts thereof.

In another aspect, provided herein is a method of treating myelofibrosis comprising administering to a subject in need thereof 2-amino-N-(4-hydroxy-bicyclo-[2.2.2]octan-1-yl)-5-(4-((1R,5S)-3-(tetrahydro-2H-pyran-4-yl)-3-azabicyclo[3.1.0]-hexan-1-yl)phenyl)nicotinamide (Compound A), or a pharmaceutically acceptable salt thereof, and (3R)-3-cyclopentyl-3-[4-(7H-pyrrolo[2,3-d]pyrimidin-4-yl)-1H-pyrazol-1-yl]propanenitrile phosphoric acid salt.

In yet another aspect, provided herein is a method of treating polycythemia vera (PV) comprising administering to a subject in need thereof 2-amino-N-(4-hydroxy-bicyclo-[2.2.2]-octan-1-yl)-5-(4-((1R,5S)-3-(tetrahydro-2H-pyran-4-yl)-3-azabicyclo[3.1.0]-hexan-1-yl)-phenyl)nicotinamide (Compound A), or a pharmaceutically acceptable salt thereof, and (3R)-3-cyclopentyl-3-[4-(7H-pyrrolo[2,3-d]pyrimidin-4-yl)-1H-pyrazol-1-yl]propanenitrile, or pharmaceutically acceptable salts thereof.

In another aspect, provided herein is a method of treating polycythemia vera (PV) comprising administering to a subject in need thereof 2-amino-N-(4-hydroxy-bicyclo-[2.2.2]-octan-1-yl)-5-(4-((1R,5S)-3-(tetrahydro-2H-pyran-4-yl)-3-azabicyclo[3.1.0]-hexan-1-yl)-phenyl)nicotinamide (Compound A), or a pharmaceutically acceptable salt thereof, and (3R)-3-cyclopentyl-3-[4-(7H-pyrrolo[2,3-d]pyrimidin-4-yl)-1H-pyrazol-1-yl]propanenitrile phosphoric acid salt.

In yet another aspect, provided herein is a method of treating myelofibrosis (MF) comprising administering to a subject in need thereof an ALK2 inhibitor that is a compound of Formula II:

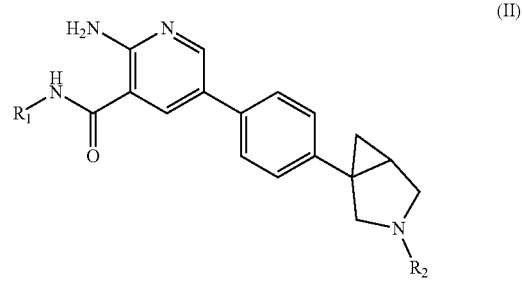

(II)

or a pharmaceutically acceptable salt thereof;
wherein
$R_1$ is bridged 5-10 membered cycloalkyl optionally substituted one, two, or three times with hydroxyl or $C_1$-$C_3$ alkoxy;

$R^2$ is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with $R^3$; and $R^3$ is selected from the group consisting of hydroxy, halo, cyano, nitro, $SO_2$—$C_1$-$C_3$; wherein the compound of Formula II is administered as a monotherapy.

In an embodiment of the method of treating myelofibrosis (MF), the compound of Formula II is 2-amino-N-(4-hydroxy-bicyclo-[2.2.2]octan-1-yl)-5-(4-(3-(tetrahydro-2H-pyran-4-yl)-3-aza-bicyclo[3.1.0]-hexan-1-yl)phenyl)nicotinamide, or a pharmaceutically acceptable salt thereof.

In an embodiment of the method of treating myelofibrosis (MF), the compound of Formula II is 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)nicotinamide, or a pharmaceutically acceptable salt thereof.

In another embodiment of the method of treating myelofibrosis (MF), the compound of Formula II is 2-amino-N-(4-hydroxybicyclo-[2.2.2]octan-1-yl)-5-(4-((1S,5R)-3-(tetrahydro-2H-pyran-4-yl)-3-azabicyclo-[3.1.0]hexan-1-yl)phenyl)nicotinamide, or a pharmaceutically acceptable salt thereof.

In an embodiment of the method of treating myelofibrosis (MF), the compound of Formula II is 2-amino-N-(4-hydroxy-bicyclo-[2.2.2]octan-1-yl)-5-(4-((1R,5S)-3-(tetrahydro-2H-pyran-4-yl)-3-azabicyclo[3.1.0]-hexan-1-yl)phenyl)nicotinamide fumarate dihydrate.

In still another aspect, provided herein is a method of treating a JAK2-associated disorder comprising administering to a subject in need thereof a JAK2 inhibitor and an ALK2 inhibitor.

In an embodiment of the methods, the JAK2-associated disorder is selected from the group consisting of polycythemia vera, graft versus host disease, allograft rejection, atopic dermatitis, psoriasis, skin sensitization, skin irritation, skin rash, contact dermatitis, allergic contact sensitization, pemphigus vulgaris (PV), and bullous pemphigoid (BP).

In an embodiment of the methods, the method involves the administration of a therapeutically effective amount of a combination or composition comprising compounds provided herein, or pharmaceutically acceptable salts thereof, to a subject (including, but not limited to a human or animal) in need of treatment (including a subject identified as in need).

In another embodiment of the methods, the treatment includes co-administering the amount of the ALK2 inhibitor and the amount of the JAK2 inhibitor. In an embodiment, the amount of the ALK2 inhibitor and the amount of the JAK2 inhibitor are in a single formulation or unit dosage form. In still other embodiments, the amount of the ALK2 inhibitor and the amount of the JAK2 inhibitor are in a separate formulations or unit dosage forms.

In the foregoing methods, the treatment can include administering the amount of ALK2 inhibitor and the amount of JAK2 inhibitor at substantially the same time or administering the amount of ALK2 inhibitor and the amount of JAK2 inhibitor at different times. In some embodiments of the foregoing methods, the amount of ALK2 inhibitor and/or the amount of JAK2 inhibitor is administered at dosages that would not be effective when one or both of ALK2 inhibitor and JAK2 inhibitor is administered alone, but which amounts are effective in combination.

In some embodiments, the method or treatment reduces hepcidin serum levels in patients relative to baseline, compared to normal levels in patients, or compared to levels in patients treated with the JAK2 inhibitor alone. The hepcidin serum levels can be reduced by more than about 5%, 10%, 20%, 30%, 40%, 50%, 60%, 70%, 80%, 90% or about 100%. In some embodiments, the hepcidin serum levels are reduced by about 50% or more relative to baseline. In some embodiments, the hepcidin serum levels are reduced to less than about 150 ng/mL, 140, 130, 120, 110, 100, 90, 80, 70, 60 or about 50 ng/mL. Hepcidin levels can be tested by standard techniques, including radioimmunoassays, ELISA, ligand binding assay or mass spectrometry.

In some embodiments, the method or treatment increases serum iron concentration in patients relative to baseline, compared to normal levels in patients or compared to levels in patients treated with the JAK2 inhibitor alone. The serum iron concentration can be increased by more than about 5%, 10%, 20%, 30%, 40%, 50%, 60%, 70%, 80%, 90% or about 100%. Serum iron concentration can be tested by standard techniques.

In some embodiments, the method or treatment increases hemoglobin serum levels in patients relative to baseline, compared to normal levels in patients or compared to levels in patients treated with the JAK2 inhibitor alone. The hemoglobin serum levels can be increased by more than about 5%, 10%, 15%, 20%, 25% or about 30%. Hemoglobin levels can be tested by standard techniques.

In some embodiments, the method or treatment increases transferrin saturation (TSAT) in patients relative to baseline, compared to normal levels in patients or compared to levels in patients treated with the JAK2 inhibitor alone. The TSAT can be increased by more than about 5%, 10%, 15%, 20%, 25% or about 30%. TSAT can be tested by standard techniques.

In some embodiments, the method or treatment reduces ferritin blood levels in patients relative to baseline, compared to normal levels in patients, or compared to levels in patients treated with the JAK2 inhibitor alone. The ferritin blood levels can be reduced by more than about 5%, 10%, 20%, 30%, 40%, 50%, 60%, 70%, 80%, 90% or about 100%. Ferritin blood levels can be tested by standard techniques.

Package Formulations

Packaged pharmaceutical formulations or pharmaceutical products are included herein. Such packaged formulations include one or more pharmaceutical formulations comprising a combination of an ALK2 inhibitor and a JAK2 inhibitor. The combination of compounds in formulated form is contained in a container. The package typically contains instructions for using the formulation to treat an animal (typically a human patient) suffering from cancer or a JAK2-associated disorder.

In certain embodiments the packaged pharmaceutical formulation or pharmaceutical product contains the combination of compounds described herein in a container with instructions for administering the dosage forms on a fixed schedule. In some of these embodiments, the combination of compounds is provided in separate unit dosage forms.

In a particular embodiment, the compounds of the combination can be dosed on the same schedule, whether by administering a single formulation or unit dosage form containing all of the compounds of the combination, or by administering separate formulations or unit dosage forms of the compounds of the combination. However, some of the compounds used in the combination may be administered more frequently than once per day, or with different frequencies that other compounds in the combination. Therefore, in one embodiment the packaged pharmaceutical formation contains a formulation or unit dosage form containing all of the compounds in the combination of compounds, and an additional formulation or unit dosage form that includes one of the compounds in the combination of agents, with no additional active compound, in a container, with instructions for administering the dosage forms on a fixed schedule.

The package formulations provided herein include comprise prescribing information, for example, to a patient or health care provider, or as a label in a packaged pharmaceutical formulation. Prescribing information may include for example efficacy, dosage and administration, contraindication and adverse reaction information pertaining to the pharmaceutical formulation.

In all of the foregoing the combination of compounds of the invention can be administered alone, as mixtures, or with additional active agents.

Administration/Dosage/Formulations

In another aspect, provided herein is a pharmaceutical composition or pharmaceutical combination comprising the compounds disclosed herein, together with a pharmaceutically acceptable carrier.

Administration of the combination includes administration of the combination in a single formulation or unit dosage form, administration of the individual agents of the combination concurrently but separately, or administration of the individual agents of the combination sequentially by any suitable route. The dosage of the individual agents of the combination may require more frequent administration of one of the agent(s) as compared to the other agent(s) in the combination. Therefore, to permit appropriate dosing, packaged pharmaceutical products may contain one or more dosage forms that contain the combination of agents, and one or more dosage forms that contain one of the combination of agents, but not the other agent(s) of the combination.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms are dictated by and directly dependent on (a) the unique characteristics of the disclosed compound and the particular therapeutic effect to be achieved, and (b) the limitations inherent in the art of compounding/formulating such a disclosed compound for the treatment of pain, a depressive disorder, or drug addiction in a patient.

In one embodiment, the compounds provided herein are formulated using one or more pharmaceutically acceptable excipients or carriers. In one embodiment, the pharmaceutical compositions provided herein comprise a therapeutically effective amount of a disclosed compound and a pharmaceutically acceptable carrier.

The drug compounds provided herein (for example, an ALK2 inhibitor and a JAK2 inhibitor) are present in the combinations, dosage forms, pharmaceutical compositions and pharmaceutical formulations disclosed herein in a ratio in the range of 100:1 to 1:100. For example, the ratio of a JAK2 inhibitor: an ALK2 inhibitor can be in the range of 1:100 to 1:1, for example, 1:100, 1:90, 1:80, 1:70, 1:60, 1:50, 1:40, 1:30, 1:20, 1:10, 1:5, 1:2, or 1:1 of JAK2 inhibitor: ALK2 inhibitor. In another example, the ratio of an ALK2 inhibitor: a JAK2 inhibitor can be in the range of 1:100 to 1:1, for example, 1:100, 1:90, 1:80, 1:70, 1:60, 1:50, 1:40, 1:30, 1:20, 1:10, 1:5, 1:2, or 1:1 of an ALK2 inhibitor: a JAK2 inhibitor.

The optimum ratios, individual and combined dosages, and concentrations of the drug compounds that yield efficacy without toxicity are based on the kinetics of the active ingredients' availability to target sites, and are determined using methods known to those of skill in the art.

Routes of administration of any of the compositions discussed herein include oral, nasal, rectal, intravaginal, parenteral, buccal, sublingual or topical. The compounds may be formulated for administration by any suitable route, such as for oral or parenteral, for example, transdermal, transmucosal (e.g., sublingual, lingual, (trans)buccal, (trans) urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In one embodiment, the preferred route of administration is oral.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions are not limited to the particular formulations and compositions that are described herein.

For oral application, particularly suitable are tablets, dragees, liquids, drops, suppositories, or capsules, caplets and gel caps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings of the present disclosure as set forth.

EXAMPLES

The compounds and methods disclosed herein are further illustrated by the following examples, which should not be construed as further limiting. The practice of the present disclosure will employ, unless otherwise indicated, conventional techniques of organic synthesis, cell biology, cell culture, and molecular biology, which are within the skill of the art.

Processes for preparing the compounds disclosed herein can be found, at least, in WO 2018/014829 and WO 2010/083283, the contents of which are incorporated in their entirety.

Example 1: Turpentine-Induced Anemia

C57Bl/6 mice (7-8-week-old, female) were purchased from Charles River Laboratories, Wilmington, Mass., and placed on low iron chow (Test Diet #AIN-76A 5TJK) two weeks prior to beginning study. Mice were continued on this diet through the course of the study. Mice were injected subcutaneously in the intrascapular region of the back of the recipient mouse with sterile filtered turpentine (Aldrich, cat #24245), or sterile saline in a 100 ul volume every week for three weeks. Therapeutic agents were orally administered at a total volume of 10 mL/kg body weight. Mice were administered vehicle (0.5% DMAC: 95% methylcellulose) or compound (n=10 per dose group) starting shortly after the first turpentine injection (day 0), and continuing every day until the study termination. Blood was collected via by orbital sinus once weekly, and complete blood counts (CBCs) were determined by hematology instrumentation (Abaxis, model HM5). Statistical analyses were performed using Graphpad Prism software. Mice were handled according to Incyte IACUC protocols.

Figure 2:
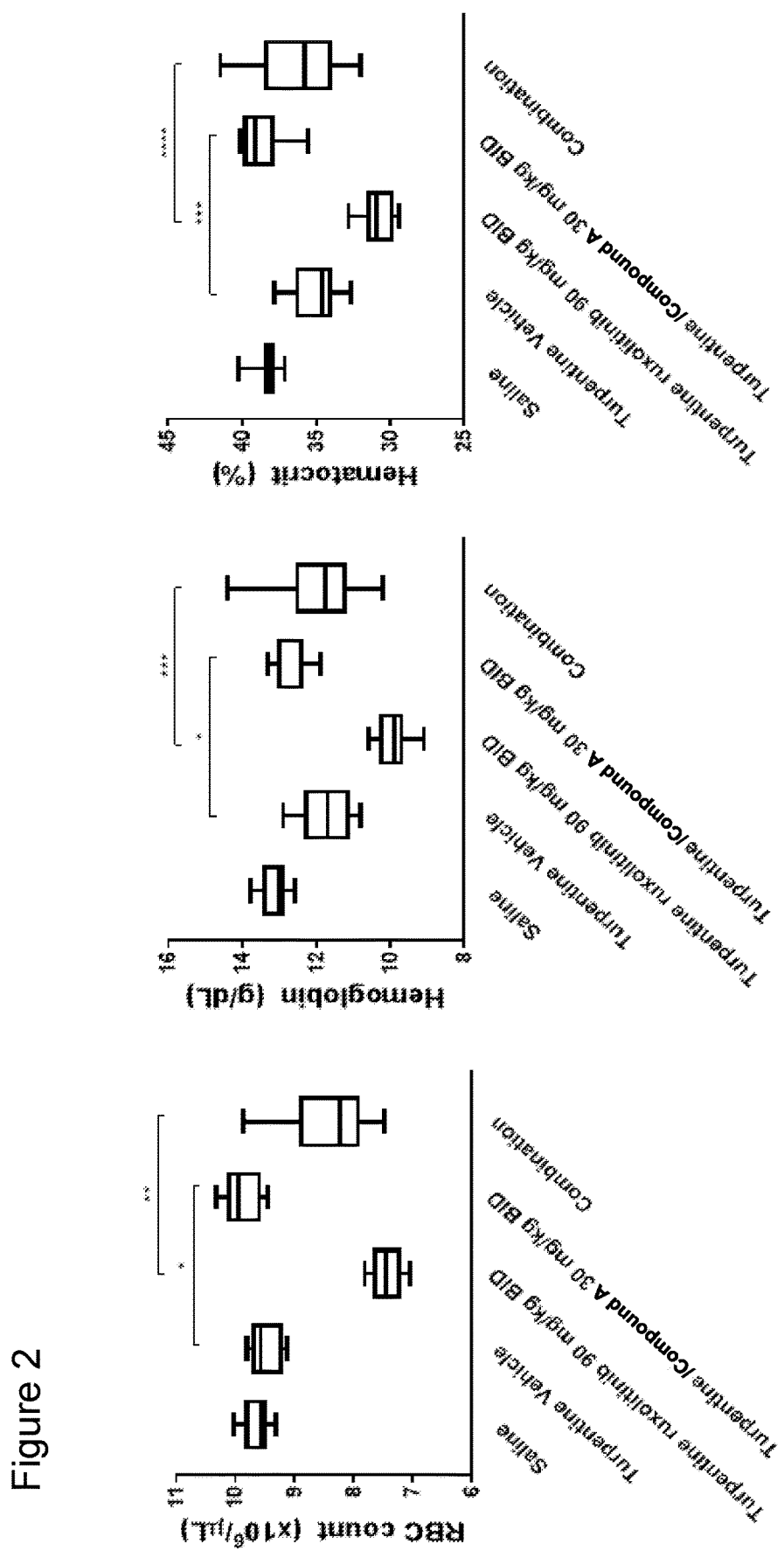
FIG. 2 shows how 30 mg/kg BID of a Compound of Formula II corrects anemia in mice brought on by turpentine alone, or in combination with a Compound of Formula I.

In each of the experiments performed, the ALK2 inhibitor (Compound A, 2-amino-N-(4-hydroxybicyclo[2.2.2]octan-1-yl)-5-(4-(3-(tetrahydro-2H-pyran-4-yl)-3-azabicyclo [3.1.0]-hexan-1-yl)phenyl)nicotinamide) (100 mg/kg QD) corrected the anemia brought on by turpentine. In FIG. 1, Compound A improved the red blood cell count, hemoglobin, and hematocrit to levels similar to saline (non-turpentine induced anemia) control at 28 days post first turpentine injection. In FIG. 2, with Compound A dosed at 30 mg/kg BID, the same trend was demonstrated by day 21 post first turpentine injection, and the change was statistically significant (*$p<0.05$; $p<0.01$; *$p<0.001$; **$p<0.0001$ as determined by unpaired t-test). Also, the JAK2 inhibitor (ruxolitinib, 3-cyclopentyl-3-[4-(7H-pyrrolo[2,3-d]-pyrimidin-4-yl)-1H-pyrazol-1-yl]propanenitrile) (90 mg/kg BID) exacerbated the anemias brought on by turpentine injection in each experiment, most likely due to the pan-cytopenic effects of JAK2 inhibition in mice. Compound A improved the blood parameters of mice that were also dosed with ruxolitinib, with significant increases in RBC, hemoglobin, and hematocrit levels in FIG. 2**. Together these experiments indicate that ALK2 inhibition can reverse the decreases in RBC counts, hemoglobin, and hematocrit brought on by turpentine generated, inflammation induced anemia, and this anti-anemia efficacy from ALK2 inhibition is possible in the presence of ruxolitinib.

Example 2: Clinical Protocol

A study of the ALK2 inhibitor administered as a monotherapy or in combination with the JAK2 inhibitor is performed in adult participants with anemia due to myeloproliferative or myelodysplastic hematological malignancies.

Overall study design. Phase I/II study open-label, multi-center, dose-escalation and expansion, safety and preliminary efficacy study of Compound A administered as a monotherapy or in combination with ruxolitinib in subjects with anemia (defined as Hgb<10 g/dL) due to myeloproliferative or myelodysplastic hematological malignancies. For both the monotherapy and the combination portions, each participant will be observed for at least one treatment cycle (28 days).

Part 1: Monotherapy portion including both the dose-escalation and the expansion stages where Compound A is administered alone in subjects with anemia due to lower-risk myelodysplastic syndromes (MDS). Combination portion including the dose-escalation stage where Compound A is administered in combination with ruxolitinib in subjects with primary myelofibrosis (PMF), post polycythaemia vera (PV) or post essential thrombocythaemia (ET) myelofibrosis and presenting anemia; collectively called "MF" subjects.

Part 2: Combination portion including only the expansion stage where Compound A is administered in combination with ruxolitinib in MF subjects.

Both the monotherapy and the combination portions are divided in 2 stages. The dose-escalation stage will determine the maximum tolerated doses (MTDs), the recommended expansion phase doses (REPDs) that will be taken forward in the corresponding expansion portions and the biologically active dose (BAD) defined as the tolerated dose(s) that produce evidence of biological effect of the explored dose (s)/regimen(s). The expansion stage will evaluate the safety, efficacy, PK, and PD of the REPD selected in the dose-escalation stages (monotherapy and combination portions) from the corresponding treatment groups.

Three (3) different treatment groups are provided. For the monotherapy portion, only 1 treatment group is provided: Treatment Group A (TGA) including subjects with anemia due to lower-risk myelodysplastic syndromes (MDS). For the combination portion, two different treatment groups are defined among subjects with anemia due to MF: Treatment Group B (TGB) including MF subjects with anemia on a stable dose of ruxolitinib for at least 8 weeks of treatment (acceptable starting doses are 10 mg twice daily [BID], 15 mg BID, 20 mg BID and 25 mg BID); and Treatment Group C (TGC) including JAK-treatment naïve MF subjects with anemia. Treatment may continue as long as subjects are receiving benefit from the study treatment(s) and have not met any criteria for permanent treatment discontinuation.

The primary objectives of each part of study include, for Part 1 (Dose-escalation stages of the monotherapy and the combination portions (all treatment groups) and Expansion stage of the monotherapy portion) evaluation of the safety and tolerability of Compound A administered alone or in combination with ruxolitinib. For Part 2 (Expansion stages of the combination portion—TGB and TGC only) evaluation of the efficacy of Compound A administered in combination with ruxolitinib. Secondary objectives applicable to all treatment groups include evaluation of PD parameters (including the hepcidin blood levels), PK parameters of Compound A and of ruxolitinib where applicable, for the expansion stage of the monotherapy and the combination portions the efficacy based on response criteria applicable to MDS patients.

The overall design of the study includes a screening part for up to 28 days to confirm the subjects' eligibility, a treatment part as long as the subjects benefit from study drug(s) therapy and do not present any study drug(s) treatment discontinuation criterion, and a follow-up part for survival/long-term outcomes after permanent discontinuation of study drug(s) up to study closure.

Compound A is administered orally as a tablet/capsule. Starting doses may vary from about a daily amount of about 10 to about 50 mg, including a starting dose of about 25 mg QD or about 30 mg QD. Dose escalation is based on type and severity of toxicity and the PK/PD results observed. Administration may range from a daily amount of about 10 to about 150 mg, including about 15, 20, 25, 30, 35, 40, 45, 50, 55, 60, 65, 70, 75, 80, 85, 90, 95, 100, 105, 110, 115, 120, 125 and about 150 mg.

For TGB and TGC groups, ruxolitinib is administered continuously per oral route as a tablet twice daily (BID). For TGC, the starting dose is about 15 mg BID if the subject's platelet value is between 100 and $200 \times 10^9$/L. The starting dose is about 20 mg BID if the subject's platelet value is greater than $200 \times 10^9$/L. During treatment by ruxolitinib and according to the disease response and hematology toxicity experienced by the subjects, additional doses include 5 mg, 10 mg, 15 mg, 20 mg and 25 mg BID. Dose escalation is based on type and severity of toxicity and the PK/PD results observed.

The following laboratory testing is performed on subject samples. Iron metabolism (measurements to be performed centrally) is tested in the chemistry panel, including serum hepcidin, serum iron, serum ferritin & ferritin index [FTI], ferritin saturation, serum transferrin, transferrin saturation, total iron binding capacity (TIBC), unsaturated iron binding capacity (UIBC), serum non-transferrin-bound iron (NTBI), soluble serum transferrin receptor (sTFR), and growth differentiation factor 15 (GDF-15)=Bone morphogenetic protein (BMP) receptor. Hematological parameters are tested as part of the hematology panel, including reticulocytes, nucleotide red blood cell, erythrocyte hemoglobin, erythropoietin (EPO), mean corpuscular volume (MCV), mean corpuscular hemoglobin (MCH), and myeloblasts in peripheral blood. Additional markers of inflammation are tested as part of the biochemistry panel, including C-reactive protein (CRP), and cytokine panel including Interleukin (IL)-1, IL-2 & IL-2 receptor (IL-2R), IL-6, IL-8 & IL-22.

Inclusion Criteria: Inclusion criteria for the treatment groups A, B and C include the following:
  Ability to comprehend and willingness to sign a written informed consent form (ICF) for the study,
  Aged of 18 years or older at the time of signing the informed consent,
  Histologically-confirmed disease,
  Participant with anemia due to MDS or MF defined as:
    a. a hemoglobin [Hgb] value<10 g/dL out of the influence of red blood cell (RBC) transfusions; considering a 2-week washout period must be demonstrated during screening recorded on three (3) separate occasions with at least seven (7) days between measurements, or
    b. Participant who has received at least four (4) units of RBC transfusions during the 28 days immediately preceding Cycle 1 Day 1 OR has received an average of at least four (4) units of RBC transfusions in the eight (8) weeks immediately preceding Cycle 1 Day 1, for a hemoglobin level of <8.5 g/dL, in the absence of bleeding or treatment-induced anemia. In addition, the most recent transfusion episode must have occurred in the 28 days prior to Cycle 1 Day 1. Note: the latter option corresponds to the definition of a transfusion-dependent participant at baseline.

Eastern Cooperative Oncology Group (ECOG) performance status score of:
  a. 0 or 1 for the dose-escalation portions (monotherapy and combination portions),
  b. 0, 1 or 2 for the expansion portions (monotherapy and combination portions), Life expectancy greater than 6 months, Willingness to undergo a pretreatment and regular on-study bone marrow biopsies and/or aspirates (as appropriate to disease). If a biopsy and aspirate are not possible or contraindicated, or the tissue requirement cannot be satisfied, this requirement may be waived with approval from the Sponsor's medical monitor.

Willingness to avoid pregnancy or fathering children based on the following criteria:
  (i) Postmenopausal woman (i.e., surgically sterile with a hysterectomy and/or bilateral oophorectomy OR ≥12 months of amenorrhea and at least 50 years of age.)
  (ii) Woman of childbearing potential who has a negative serum pregnancy test at screening and prior to the first dose on Day 1 who agrees to take appropriate precautions to avoid pregnancy (with at least 99% certainty) from screening through safety follow-up. Permitted methods that are at least 99% effective in preventing pregnancy should be communicated to the subject and their understanding confirmed.
  (iii) Man who agrees to take appropriate precautions to avoid fathering children (with at least 99% certainty) from screening through safety follow-up. Permitted methods that are at least 99% effective in preventing pregnancy should be communicated to the subject and their understanding confirmed.

Inclusion Criteria Defining the Disease Characteristics:
  Subject with peripheral blood myeloblast count <10%.
  Subject not requiring cytoreductive therapy or a therapeutic intervention.

For Treatment Group A (TGA)
Additional inclusion criteria for the treatment groups A include a confirmed diagnosis of myelodysplastic syndrome (MDS) according to the 2016 World Health Organization (WHO) criteria (Swerdlow et al, 2017 and Arber et al, Blood, 2016).

For the myelodysplastic syndrome (MDS) subjects: very-low, low or intermediate MDS as defined by the IPSS-R criteria (Greenberg et al, Blood, 2012), except subjects presenting with myelodysplastic syndrome with ring sideroblasts (MDS-RS), OR For the MDS/MPN overlap syndrome subjects:
  i. Low or intermediate chronic myelomonocytic leukemia (CMML) according to Patnaik et al, 2013, or
  ii. Favorable or intermediate unclassifiable MDS/MPN overlap syndromes (MDS/MPN, unclassifiable) as per Liu et al, 2012 criteria,
  iii. Except participants presenting with atypical chronic myeloid leukemia (aCML), juvenile myelomonocytic leukemia (JMML) or MDS/MPN with ring sideroblasts and thrombocytosis (MDS/MPN-RS-T).

For Treatment Groups B and C (TGB and TGC):
Additional inclusion criteria for the treatment Groups B and C (TGB and TGC) include a histologically-confirmed diagnosis of primary myelofibrosis (PMF), post polycythaemia vera (PV) or post essential thrombocythaemia (ET) myelofibrosis according to the 2016 World Health Organization criteria (Swerdlow et al, 2017 and Passamonti et al, ASH publications, 2016 for PMF and Barosi et al, Leukemia, 2008 for post-ET and post-PV myelofibrosis) and prior treatment.

For TGB, each subject must have been on a therapeutic and stable regimen of ruxolitinib (10 mg, 15 mg, 20 mg or 25 mg BID) for at least eight (8) consecutive weeks immediately preceding the first treatment dose in the study, and each subject for whom the dose and dose-regimen of ruxolitinib to treat MF has not been modified at any time during the 8 weeks immediately preceding the 1st treatment dose in the study.

For TGC, each subject must be naïve of any treatment by any JAK inhibitor.

Exclusion Criteria: Exclusion criteria for the treatment groups A, B and C include the following:

Subjects with laboratory values at screening as defined in Table 1.

TABLE 1

Exclusionary Laboratory Values

| | Laboratory Parameter | Exclusion Criterion |
|---|---|---|
| | Hematology | |
| a | Platelets | For TGA participants: <50 × $10^9$/L without the assistance of growth factors, thrombopoietic factors or platelet transfusions For TGB and TGC participants: <100 × $10^9$/L without the assistance of growth factors, thrombopoietic factors or platelet transfusions |
| b | Absolute neutrophil count (ANC) | For TGA participants: <0.75 × $10^9$/L For TGB and TGC participants: <1.0 × $10^9$/L |
| | Hepatic | |
| c | Alanine aminotransferase (ALT) | ≥2.5 × ULN |
| d | Aspartate aminotransferase (AST) | ≥2.5 × ULN |
| e | Direct bilirubin | >2.0 × ULN |
| f | Alkaline phosphatase (ALP) | ≥3 × ULN |
| | Renal | |
| g | Creatinine clearance | <30 mL/min according to Cockcroft-Gault formula. |

TGA, TGB, and TGC = treatment group A, B, and C, ULN = upper limit of normal.

Subject with any major surgery within 28 days prior to the first study treatment, Any prior chemotherapy, immunomodulatory drug therapy, immunosuppressive therapy, biological therapy, endocrine therapy, targeted therapy, antibody, erythropoietin-stimulating agent (ESA), hypomethylating agent, or granulocyte colony stimulating factor [G-CSF], granulocyte/macrophage colony stimulating factor [GM-CSF], romiplostin, eltrombopag, folic acid (folate), or vitamin B12 (cobalamin) to treat the subject's disease with the exception of ruxolitinib for TGB only within 5 half-lives or 28 days (whichever is shorter) prior to the first study treatment. Subject undergoing treatment with another investigational medication or having been treated with an investigational medication within 28 days prior to screening, Subject undergoing treatment within 28 days or 5 half-lives (whichever is longer) of the first study treatment with a potent/strong inhibitor or inducer of CYP3A4/5, or expected to receive such treatment during the study.

Any prior radiation therapy within 28 days or 5 half-lives (whichever is longer) of the first study treatment. Palliative radiation therapy to single sites or small fields allowed with at least one (1) week washout prior to the first study treatment.

Any prior allogenic or autologous transplantation, or the subject is a candidate for an allogenic or autologous transplantation, History of leukocytosis (history of WBC>25×$10^9$/L), Presence of any hematological malignancy other than MDS or MF, Active invasive malignancy over the previous 5 years except subjects with early-stage basal cell or squamous cell skin cancer, or completely resected intraepithelial carcinoma of the cervix, or completely resected papillary thyroid and follicular thyroid cancers who may be eligible participate at the Investigator's discretion. Subjects with malignancies with indolent behavior such as prostate cancer treated with radiation or surgery may be enrolled as long as they have a reasonable expectation to have been cured with the treatment modality received, Known active disease involving the central nervous system (CNS), for example, brain metastasis or spinal cord compression, except primary CNS lymphoma, History of clinically significant or uncontrolled cardiac disease, including recent (within the last 12 months) unstable angina or acute myocardial infarction, or New York Heart Association Class III or IV congestive heart failure, or clinically significant arrhythmias not controlled by medication. Subjects with a pacemaker and well controlled rhythm for at least 1 month before the first dose of study medication will be allowed, History or presence of an abnormal ECG that, in the investigator's opinion, is clinically meaningful. Screening QTc interval >450 milliseconds is excluded. For subjects with an intraventricular conduction delay (QRS interval 120 ms), the JTc interval may be used in place of the QTc with sponsor approval. Subjects with left bundle branch block are excluded. Subjects with QTc prolongation due to a pacemaker may enroll with prior approval from the sponsor's medical monitor, Presence of chronic or current active infectious disease requiring systemic antibiotic, antifungal, or antiviral treatment. Subjects with acute bacterial infection requiring antibiotic use should delay screening/enrollment until the course of antibiotic therapy has been completed and the infection is not active anymore, Subject with diagnosis of chronic liver disease (e.g., chronic alcoholic liver disease, autoimmune hepatitis, sclerosing cholangitis, primary biliary cirrhosis, hemochromatosis, non-alcoholic steatohepatitis), Subject with known active hepatitis A, hepatitis B virus (HBV), or hepatitis C virus (HCV) infection or who are HIV-positive, Unwillingness to be transfused with blood components including red blood cell packs and platelet transfusions, Subjects who, in the opinion of the investigator, are unable or unlikely to comply with the dose schedule and study evaluations, Any condition in the investigator's judgment that would interfere with full participation in the study, including administration of study drug and attending required study visits; pose a significant risk to the subject; or interfere with interpretation of study data, Active alcohol or drug addiction that would interfere with their ability to comply with the study requirements, Gastroesophageal reflux disease not controlled by medication (i.e., currently symptomatic or endoscopic evidence of esophagitis) within 28 days prior to first study drug(s) dose, Has any unresolved toxicity ≥Grade 2 from previous therapy except for stable chronic toxicities (≤Grade 2) not expected to resolve, such as stable Grade 2 peripheral neuropathy, Subject has known hypersensitivity or severe reaction, or any known contraindications to the use to any of the active substances or excipients in Compound A or ruxolitinib or similar compounds as appropriate to the relevant treatment group, Females who are pregnant or currently breastfeeding,
Unable to swallow and retain oral medication, and
Unable to comprehend or unwilling to sign the informed consent form (ICF).

Additional exclusion criteria for Treatment Groups B and C (TGB and TGC) include a subject with any history of platelet counts <50×10$^9$/L or ANC<0.5×10$^9$/L except during treatment for a myeloproliferative disorder or treatment with cytotoxic therapy for any other reason, and any subject undergoing treatment with hematopoietic growth factor receptor agonist (i.e., erythropoietin [EPO]), granulocyte colony stimulating factor (G-CSF), romiplostin, eltrombopag at any time within 4 weeks prior to screening, and subject undergoing treatment within 14 days or 5 half-lives (whichever is longer) of 1st study drug(s) dose with a potent/strong inhibitor or inducer of CYP3A4 or expected to receive such treatment during the course of the study, and any subject unwilling or unable to undergo MRIs or CT Scans par study protocol requirements.

Primary Analyses:
Part 1: Safety Analyses for TGA—Dose Escalation and Expansion, TGB—Dose Escalation, TGC—Dose Escalation:
The safety of Compound A administered alone or in combination with ruxolitinib will be analyzed using the following parameters descriptively by part, treatment group, and dose level in safety population:

Frequency, duration, and severity of adverse events (AEs), severe adverse events (SAEs) and dose-limiting toxicity (DLTs),
Changes in vital signs and clinical evaluations including electrocardiograms (ECGs),
Clinical laboratory blood and urine sample evaluations,
The rate of DLTs will be summarized for each cohort of the dose-escalation portions.

Part 2: Efficacy Analyses for TGB—Dose Expansion, TGC—Dose Expansion:
The proportion of participants with an anemia response defined as an Hgb increase ≥1.5 g/dL for ≥12 weeks during treatment, if transfusion independent OR achieving transfusion independence for ≥12 weeks if transfusion dependent at baseline if applicable, will be estimated with its 95% confidence intervals (CI).
The proportion will be tested against 20% using a one-sample proportion test in full analysis set (FAS) population at a one-sided alpha of 5%.

Participants with missing assessments that prevent the evaluation of the primary endpoint will be considered as nonresponders on that treatment arm. No data imputation will be applied.

Secondary Analyses: Analyses of Dose-escalation stages of the monotherapy and the combination portions (all treatment groups) and Expansion stage of the monotherapy portion include efficacy, pharmacokinetics (PK), and pharmacodynamics (PD) of Compound A administered alone or in combination with ruxolitinib in the defined patient populations.

Expansion stage of the combination portion (TGB and TGC only) include safety of Compound A administered in combination with ruxolitinib in anemic MF subjects. The safety assessments will include:

PK for plasma Compound A: $C_{max}$, $t_{max}$, $AUC_{0-t}$, $AUC_{0-\infty}$, $t_{1/2}$, Cl/F, Vz/F, and λz,
PK for urine Compound A: Ae96h and CLr,
PK for saliva Compound A: $C_{max}$, $t_{max}$, $AUC_{0-t}$, $AUC_{0-\infty}$ and CLs, and
PK for metabolites of Compound A
In plasma ($C_{max}$, $t_{max}$, $AUC_{0-t}$, $AUC_{0-\infty}$), and
In urine (Ae, CLr, Fe (% excreted)),

| Abbreviation | Definition |
| --- | --- |
| $C_{max}$ | Maximum observed plasma concentration |
| $t_{max}$ | Time to maximum plasma concentration |
| $AUC_{0-t}$ | Area under the single-dose plasma concentration-time curve from Hour 0 to the last quantifiable measurable plasma concentration, calculated by the linear trapezoidal rule for increasing concentrations and the log trapezoidal rule for decreasing concentrations |
| $AU_{0-\infty}$ | Area under the steady-state plasma concentration-time curve over 1 dosing interval (i.e., from Hour 0 to 12 for BID administration or from Hour 0 to 24 for QD administration), calculated by the linear trapezoidal rule for increasing concentrations and the log trapezoidal rule for decreasing concentrations |
| Cl/F | Oral dose clearance |
| Vz/F | Apparent oral dose volume of distribution |
| λz | Apparent terminal phase disposition rate constant, where λz is the magnitude of the slope of the linear regression of the log concentration versus time profile during the terminal phase |
| Ae96h | Amount of drug excreted in the urine over sampling interval (e.g., 96 h) |
| Clr | Renal clearance, where Clr = $A_e$/AUC |
| Fe (% excreted) | Percent iron excreted in the urine, where % excreted = 100 ($A_e$/dose) |

The following PD parameters will be summarized descriptively by part, stage, treatment group, and dose level in PD evaluable population at each visit.

Plasma hepcidin levels,
PD parameters to assess the iron homeostasis: total serum iron (TSI), ferritin, transferrin, transferrin saturation (TSAT), total iron-binding capacity (TIBC), unsaturated iron-binding capacity (UIBC), non-transferrin-bound serum iron (NTBI),
PD parameters to assess the erythropoiesis: reticulocyte count (RC), nucleated red blood cell (NRBC), mean corpuscular volume (MCV), mean corpuscular hemoglobin (MCH), hemoglobin, hematocrit, red blood cell (RBC)

count, mean corpuscular hemoglobin concentration (MCHC), red blood cell distribution width (RDW), Other PD parameters: erythropoietin (EPO), Part 1 Efficacy Analyses for TGA Dose Expansion:

Percentage of participants with hematological improvement for erythroid line (HI-E), for platelets (HI-P), and for neutrophils (HI-N) as per Cheson et al, 2006, definitions will be estimated with 95% $C_1$.

Mean change from baseline in the Hgb value over 4-week treatment periods will be summarized descriptively.

Percentage of participants with 50% reduction in transfusion burden as compared to baseline in any 8-week window during treatment period will be estimated.

Percentage of participants with complete response (CR) or partial response (PR) as per Cheson et al, 2006 definitions for myelodysplastic syndromes, or as per the Savona et al, 2015 definitions for the MDS/MPN overlap syndromes as applicable will be estimated with 95% $C_1$.

Progression-free survival (PFS) defined as the interval from the first dose of Compound A until the first documentation of definitive disease progression (as per Cheson et al, 2006 definitions for myelodysplastic syndromes or Savona et al, 2015 definitions for MDS/MPN overlap syndromes) or death due to any cause will be estimated using Kaplan-Meier method.

Leukemia-free survival (LFS), defined as the interval from the first dose of Compound A until the first documented leukemia transformation (a blast percentage of ≥20% in the bone marrow or the peripheral blood at any time during the study) or death from any cause will be estimated using Kaplan-Meier method.

For transfusion-dependent (TD) participants at screening:

Percentage of participants with reduction of units of RBC transfusions by an absolute number of ≥4 RBC transfusions/8 week compared with the pretreatment transfusion number in the previous eight (8) weeks if applicable as per Cheson et al, 2006, will be estimated.

Percentage of participants with red blood cell-transfusion independency (RBC-TI) defined as the absence of any RBC-transfusion for at least eight consecutive weeks during the treatment period will be estimated.

Part 2 Safety Analyses for TGB and TGC Dose Expansion:

The safety of Compound A administered in combination with ruxolitinib will be analyzed using the following parameters descriptively by treatment group, and dose level in safety population:

Frequency, duration, and severity of AEs and SAEs,

Changes in vital signs, ECGs, and physical examinations,

Changes in clinical blood and urine laboratory parameters.

Part 2 Efficacy Analyses for TGB and TGC Dose Expansion:

Anemia response

Duration of anemia response, defined as

The interval from the first onset of Hgb increase ≥1.5 g/dL for ≥12 weeks to the earliest date of loss of anemia response that persists for at least four (4) weeks, or death from any cause for the TI participants at baseline, or Duration of transfusion-independence is defined as the interval from the first onset date of transfusion independence to the earliest onset date of transfusion dependence or death from any cause for the TD participants at baseline, will be estimated separately for transfusion dependent (TD) and transfusion-independent (TI) participants at baseline using Kaplan-Meier method with 95% $C_1$.

Mean change from baseline in the Hgb value over 12-week treatment periods will summarized descriptively.

Rate of RBC-transfusion through Weeks 24 and 48 defined as the average number of RBC units per participant-month during treatment. The proportion of participants receiving RBC transfusions over each month post baseline period will be estimated, and the total number of RBC units received per participant over each month post baseline period will be calculated.

The splenic response rate at Week 24 (SSR24) defined as the proportion of participants achieving a ≥35% reduction in spleen volume at Week 24 relative to baseline as measured by MRI or CT scan, will be estimated with 95% CI.

Spleen length response defined as the proportion of participants achieving a ≥50% reduction in spleen length at any visit relative to baseline as measured by palpation will be estimated.

Symptom response rate at Week 24 defined as the proportion of participants who achieve a ≥50% reduction in total symptom score (TSS) at Week 24 relative to baseline as measured by the Myelofibrosis Symptom Assessment Form (MFSAF) v 4.0 form (Gwaltney et al, 2017), will be estimated.

Percentage of participants with CR or PR according to the Tefferi et al, 2013 definitions will be estimated with 95% $C_1$.

The morphologic effects of the combination of Compound A with ruxolitinib on bone marrow will be summarized descriptively.

Progression-free survival (PFS) defined as the interval from the first dose of study treatment until the first documentation of definitive disease progression or death due to any cause as per the Tefferi et al, 2013 definitions, will be estimated with the Kaplan Meier method.

Leukemia-free survival (LFS) defined as the interval from the first dose of Compound A until the first documented leukemia transformation or death from any cause, will be estimated with the Kaplan Meier method.

For PFS, the earliest time when any event is observed as follows:

For spleen volume increase, the progression date will be the date of the first MRI showing a 25% or greater increase in spleen volume as compared to the on-study nadir (the on study period includes the Baseline evaluation), For splenic irradiation, splenectomy, or death, the date of progression will be the actual date of the event, For leukemic transformation:

Determined by bone marrow blast count of 20% or greater, the progression date will be the date of the bone marrow aspirate or biopsy as applicable, Determined by peripheral blast count, the date of progression will be the date of the first peripheral blast count of 20% or greater that is subsequently confirmed by EITHER eight (8) weeks of sustained high blast counts [i.e., no intervening counts of <20%] OR by bone marrow aspirate/biopsy.

Part 2 Safety Analyses for TGB and TGC Dose Expansion: The safety assessments will be identical to those in the dose-escalation portions.

Example 3: Additional Clinical Protocol for MF-Induced Anemia

This study is a phase 1/2, open-label, multicenter, dose-escalation and -expansion study assessing Compound A alone (treatment group A [TGA]) or in combination with ruxolitinib (treatment group B [TGB]), in patients with MF who are transfusion-dependent or present with symptomatic anemia. For TGA, patients must have been intolerant, resistant, refractory, or lost response to prior therapy (≥12 weeks) with Janus kinase inhibitors and have a risk category of intermediate-2 or high according to the Dynamic International Prognostic Scoring System (DIPSS); for TGB, patients must have been on a therapeutic and stable regimen of ruxolitinib for ≥12 consecutive weeks prior to first dose of study treatment and have a DIPSS risk category of intermediate-1 or -2, or high. To be eligible patients must be ≥18 years of age, have an Eastern Cooperative Oncology Group (ECOG) performance status 0-1 for the dose-escalation stages or 0-2 for the dose-expansion stage, have life expectancy >6 months, and have histologically confirmed primary or secondary (post-polycythemia vera, post-essential thrombocythemia) MF.

Patients are ineligible if they have any other hematologic malignancy; have undergone any prior allogeneic or autologous stem cell transplantation; have undergone major surgery within 28 days of first dose of study drug; or received prior chemotherapy, immunomodulatory drug, immunosuppressive, biological, endocrine, or targeted therapy, or an antibody/hypomethylating agent within 5 half-lives or 28 days before first dose of study drug.

In Part 1 (dose escalation) of the study, patients will be enrolled into TGA or TGB. Compound A monotherapy will be administered orally at a starting dose of 50 mg/day in TGA (28-day cycles). Dose-escalation stages will use a Bayesian optimal interval design to determine the maximum tolerated dose (MTD), with dose increases not exceeding 100% (2-fold) until a treatment-related toxicity Grade ≥2 is observed. Dose escalation in TGB will start 2 dose levels below the maximum evaluated dose determined to be safe and tolerable in TGA (recommended dose expansion [RDE]); patients in TGB will receive Compound A in combination with ruxolitinib. In each treatment group in Part 1, ≤24 patients will be treated in the dose-escalation stage. In Part 2 (dose expansion), the RDE in TGB will be evaluated in combination with ruxolitinib in approximately 25 patients. Patients will receive treatment for up to 12 months, and treatment may continue if patients are deriving clinical benefit and have no evidence of progressive disease.

The primary study objective is to determine the safety and tolerability of Compound A monotherapy or in combination with ruxolitinib (assessed by the frequency and severity of adverse events [AEs], physical examinations, and monitoring vital signs and laboratory values, and identification of dose-limiting toxicities, MTD, and RDE for TGB). Secondary objectives are to determine the efficacy of Compound A monotherapy or in combination with ruxolitinib (assessed by anemia response, duration of anemia response, mean change from baseline in hemoglobin, and rate of RBC transfusion through week 24 and 48), evaluate pharmacokinetics of Compound A, and evaluate the effect of Compound A as monotherapy or in combination with ruxolitinib on hepcidin level, iron homeostasis, and erythropoiesis.

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A method of treating cancer in a subject in need thereof, comprising administering to the subject an ALK2 inhibitor that is 2-amino-N-(4-hydroxybicyclo[2.2.2]octan-1-yl)-5-(4-(3-(tetrahydro-2H-pyran-4-yl)-3-azabicyclo[3.1.0]hexan-1-yl)phenyl)nicotinamide, or pharmaceutically acceptable salt thereof, and a JAK2 inhibitor that is 3-cyclopentyl-3-[4-(7H-pyrrolo[2,3-d]pyrimidin-4-yl)-1H-pyrazol-1-yl]propanenitrile or a pharmaceutically acceptable salt thereof.

2. The method of claim 1, wherein the JAK2 inhibitor is (3R)-3-cyclopentyl-3-[4-(7H-pyrrolo[2,3-d]pyrimidin-4-yl)-1H-pyrazol-1-yl]propanenitrile, or a pharmaceutically acceptable salt thereof.

3. The method of claim 1, wherein the ALK2 inhibitor is 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)nicotinamide, or a pharmaceutically acceptable salt thereof.

4. The method of claim 1, wherein the ALK2 inhibitor and JAK2 inhibitor are administered in a single formulation.

5. The method of claim 4, wherein the single formulation further comprises a pharmaceutically acceptable carrier.

6. The method of claim 1, wherein the ALK2 inhibitor and JAK2 inhibitor are administered separately.

7. The method of claim 1, wherein the cancer is a myeloproliferative neoplasm or a myelodysplastic syndrome.

8. The method of claim 7, wherein the cancer is selected from the group consisting of chronic myeloid leukemia (CML), polycythemia vera (PV), essential thrombocythemia (ET), myelofibrosis (MF), chronic neutrophilic leukemia, chronic eosinophilic leukemia, chronic myelomonocytic leukemia, juvenile myelomonocytic leukemia, hypereosinophilic syndrome, systemic mastocytosis, atypical chronic myelogenous leukemia, acute lymphoblastic leukemia (ALL), and acute myeloid leukemia (AML).

9. The method of claim 7, wherein the cancer is myelofibrosis (MF).

10. The method of claim 7, wherein the cancer is selected from the group consisting of primary myelofibrosis, post-polycythemia vera myelofibrosis, or post-essential thrombocythemia myelofibrosis.

11. The method of claim 1, wherein the treatment comprises administering the ALK2 inhibitor and the JAK2 inhibitor at different times.

12. The method of claim 1, wherein the method comprises administering to a subject in need thereof 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)nicotinamide and (3R)-3-cyclopentyl-3-[4-(7H-pyrrolo[2,3-d]pyrimidin-4-yl)-1H-pyrazol-1-yl]propanenitrile, or pharmaceutically acceptable salts thereof.

* * * * *